United States Patent
Martinelli

[19]

[11] Patent Number: 6,104,944
[45] Date of Patent: Aug. 15, 2000

[54] SYSTEM AND METHOD FOR NAVIGATING A MULTIPLE ELECTRODE CATHETER

[76] Inventor: Michael A. Martinelli, 58 Wedgemere Ave., Winchester, Mass. 01890

[21] Appl. No.: 08/972,061

[22] Filed: Nov. 17, 1997

[51] Int. Cl.[7] .......................................................... A61B 5/00
[52] U.S. Cl. ........................... 600/424; 128/899; 600/373
[58] Field of Search ...................................... 600/424, 373, 600/374, 407, 393, 433; 128/899

[56] References Cited

U.S. PATENT DOCUMENTS

| | | | |
|---|---|---|---|
| 3,439,256 | 4/1969 | Kühne et al. ............................... | 323/51 |
| 3,674,014 | 7/1972 | Tillander ............................. | 128/2.05 R |
| 3,868,565 | 2/1975 | Kuipers ................................... | 324/34 R |
| 4,173,228 | 11/1979 | Van Steenwyk et al. .............. | 128/653 |
| 4,339,953 | 7/1982 | Iwasaki ..................................... | 73/654 |
| 4,422,041 | 12/1983 | Lienau .................................... | 324/207 |
| 4,584,577 | 4/1986 | Temple ................................ | 340/870.32 |
| 4,642,786 | 2/1987 | Hansen .................................... | 364/559 |
| 4,719,419 | 1/1988 | Dawley .................................... | 324/208 |
| 4,821,731 | 4/1989 | Martinelli et al. .................. | 128/662.03 |
| 4,849,692 | 7/1989 | Blood ...................................... | 324/208 |
| 4,862,893 | 9/1989 | Martinelli ........................... | 128/662.03 |
| 4,905,698 | 3/1990 | Strohl, Jr. et al. .................. | 128/653 R |
| 4,945,305 | 7/1990 | Blood .................................. | 324/207.17 |
| 4,977,655 | 12/1990 | Martinelli ................................ | 29/25.35 |
| 5,002,058 | 3/1991 | Martinelli ................................. | 128/662 |
| 5,042,486 | 8/1991 | Pfeiler et al. ........................ | 128/653 R |
| 5,109,194 | 4/1992 | Cantaloube ........................ | 324/207.17 |
| 5,187,475 | 2/1993 | Wagener et al. .................... | 340/870.32 |
| 5,211,165 | 5/1993 | Dumoulin et al. .................... | 128/653.1 |
| 5,228,442 | 7/1993 | Imran ...................................... | 128/642 |
| 5,237,996 | 8/1993 | Waldman et al. ....................... | 128/642 |
| 5,297,549 | 3/1994 | Beatty et al. ............................ | 128/642 |
| 5,385,146 | 1/1995 | Goldreyer ................................ | 128/642 |
| 5,385,148 | 1/1995 | Lesh et al. .......................... | 128/662.06 |
| 5,391,199 | 2/1995 | Ben-Haim ................................ | 607/122 |
| 5,433,198 | 7/1995 | Desai ....................................... | 128/642 |
| 5,443,066 | 8/1995 | Dumoulin et al. .................... | 128/653.1 |
| 5,443,489 | 8/1995 | Ben-Haim ................................ | 607/115 |
| 5,445,150 | 8/1995 | Dumoulin et al. .................... | 128/653.1 |
| 5,480,422 | 1/1996 | Ben-Haim ................................ | 607/122 |
| 5,485,849 | 1/1996 | Panescu et al. .......................... | 128/699 |
| 5,487,391 | 1/1996 | Panescu ................................... | 128/699 |
| 5,487,757 | 1/1996 | Truckai et al. . | |
| 5,546,940 | 8/1996 | Panescu et al. .......................... | 128/642 |
| 5,546,949 | 8/1996 | Frazin et al. ....................... | 128/662.06 |
| 5,546,951 | 8/1996 | Ben-Haim ............................... | 128/702 |
| 5,558,091 | 9/1996 | Acker et al. ......................... | 128/653.1 |
| 5,573,533 | 11/1996 | Strul ......................................... | 606/34 |
| 5,592,939 | 1/1997 | Martinelli . | |
| 5,741,214 | 4/1998 | Ouchi et al. . | |
| 5,938,694 | 8/1999 | Jaraczewski et al. . | |
| B1 4,905,698 | 10/1991 | Strohl, Jr. et al. ................. | 128/653 R |

*Primary Examiner*—Marvin M. Lateef
*Assistant Examiner*—Shawna J Shaw
*Attorney, Agent, or Firm*—McDermott Will & Emery

[57] ABSTRACT

A method for navigating a catheter within a navigational domain includes providing a catheter including locatable electrode elements distributed along and affixed to a length of the catheter. The locatable electrode elements include at least two navigated electrode elements and one or more virtually navigable electrode elements located relative to the at least two navigated electrode elements. Location data is; provided for the at least two navigated electrode elements and location data for the one or more virtually navigable electrode elements is determined as a function of the location data for the at least two navigated electrode elements. A system for navigating a catheter within a navigational domain includes a catheter having locatable electrode elements distributed along and affixed to a length of the catheter. The locatable electrode elements includes at least two navigated electrode elements and one or more virtually navigable electrode elements located along or near an intervening portion of the length between the at least two navigated electrode elements. The system further includes one or more transmitters to project magnetic fields into the navigational domain sufficient to induce signal values within the at least two navigated electrode elements representative of the location of the at least two navigated electrode elements within the navigational domain. A controller generates location data from the induced signal values for the at least two navigated electrode elements and determines location data for the one or more virtually navigable electrode elements as a function of the location data for the at least two navigated electrode elements.

34 Claims, 12 Drawing Sheets

SYSTEM AND METHOD FOR NAVIGATING A MULTIPLE ELECTRODE CATHETER

FIELD OF THE INVENTION

The present invention relates to catheter navigation systems and methods. More particularly, the present invention pertains to the navigation of multiple electrode catheters.

BACKGROUND OF THE INVENTION

Electrophysiological catheters of various configurations are currently available which can be guided through internal spaces, e.g., a heart chamber or a vessel of a patient undergoing surgery. Such catheters, typically have one or more electrodes associated therewith for taking electrical measurements (commonly referred to as electrograms) or performing some other application specific function within the internal spaces.

Navigation systems for conventional electrophysiological catheters which have a single navigated electrode typically determine the location of a point on the catheter which is usually close to the single navigated electrode within the internal space, or a location associated with the electrode, e.g., a location at the wall of the heart or within a heart chamber. A measurement, as desired, e.g., an electrogram, is then captured for the location, or another application specific function is performed, e.g., ablation, mapping, etc. The single electrode catheter is then moved to another location to perform additional application functions, e.g., capture another measurement. In other words, a point by point acquisition process is performed. The point by point acquisition process is time consuming and the comparable data from such an acquisition process is somewhat limited by the degree to which successive patient activities, e.g., heart cycles, are identical. For example, when heart cycles are different for successively taken cardiac measurements at multiple locations, the data captured is not actually representative of the same event and therefore, not necessarily comparable, as opposed to such cardiac measurements being taken at different locations during the same heart cycle.

To eliminate such point by point acquisition using single navigated electrode catheters, multiple electrode catheters, i.e., catheters having two or more electrodes, have been deployed. For example, one such known catheter includes a three dimensional basket at the end of the catheter including electrodes along spines of the basket for positioning within the internal space. Measurements at such electrodes when in contact with the defining structure of the internal space wherein the basket is positioned are taken. However, such catheters tend to be relatively complex, and thus costly, as compared to single electrode catheters.

Various other multiple electrode catheters tend to be less costly and more easily maneuvered than complex catheters, e.g., basket catheters. One such maneuverable multiple electrode catheter includes a single flexible elongated electrode support body with multiple electrodes distributed along the length of the support body. The catheter also has a steering mechanism for selectively bending, i.e., flexing and holding, the maneuverable portion of the catheter in a shape. In such a manner, the electrodes can be placed in contact against a structure defining the internal space into which the catheter has been inserted. Each electrode is typically operably connected for taking measurements at the electrode's particular location within the internal space.

With the positioning of such an elongated multiple electrode catheter, data can be captured and gathered from all of the electrodes simultaneously without repositioning of the catheter, vastly improving the speed and quality of data gathering. However, the difficulty with respect to such a configuration is that the location of each of the multiple electrodes must be determined, i.e., each of the electrodes must be navigated, as the maneuverable portion of the catheter has been steered into a particular shape and location. In order to provide such navigation, wiring overhead and sensor electronics overhead is substantially increased. Typically, the overhead requirements necessary for providing navigation of an electrode limits navigation for most multiple electrode catheters to no more than two or three electrodes. To navigate more than two or three electrodes is particularly cost prohibitive, as well as degrading to catheter steerability because of the increased stiffness of the catheter due to the number of required wires.

As a result, a need exists for a system and/or method for effectively and efficiently navigating multiple numbers of electrodes such that the location of such electrodes within the internal space can be used as desired, e.g., mapping, ablation, etc. The present invention provides for such navigation of multiple electrodes alleviating the problems as described above and others that will become apparent from the description below.

SUMMARY OF THE INVENTION

A method for navigating a catheter within a navigational domain in accordance with the present invention includes providing a catheter including a plurality of locatable electrode elements distributed along and affixed to a length of the catheter. The plurality of locatable electrode elements include at least two navigated electrode elements and one or more virtually navigable electrode elements located relative to the at least two navigated electrode elements. Location data is provided for the at least two navigated electrode elements and location data for the one or more virtually navigable electrode elements is determined as a function of the location data for the at least two navigated electrode elements.

In one embodiment of the method, the determination of the location data for the virtually navigable electrode elements includes providing a plurality of sets of displacement coordinates for the one or more virtually navigable electrode elements. Each of the sets of displacement coordinates corresponds to a specific relative location between a selected navigated electrode element of the at least two navigated electrode elements and one or more other navigated electrode elements of the at least two navigated electrode elements. The location data for the one or more of the virtually navigable electrode elements is determined as a function of a set of displacement coordinates corresponding to a specific relative location of the at least two navigated electrode elements as represented by the location data for the at least two navigated electrode elements.

In another embodiment of the method, each of the sets of displacement coordinates represents a difference between coordinates of each of the one or more virtually navigable electrode elements and coordinates of the selected navigated electrode element of the at least two navigated electrode elements. Further, the determination of the location data for the one or more virtually navigable electrode elements includes adding the set of displacement coordinates corresponding to the specific relative location to the coordinates of the selected navigated electrode element.

In another embodiment of the method, the step of providing the plurality of sets of displacement coordinates includes holding the location of one of the navigated electrode elements at a fixed location and moving a second navigated electrode element to a plurality of locations. The locations of the one or more virtually navigable electrode elements is measured when the second navigated electrode element is at each of the plurality of locations. The plurality of sets of displacement coordinates are generated based on the measured locations of the one or more virtually navigable electrode elements.

In another Embodiment of the method, the one or more virtually navigable electrode elements are distributed and affixed to an intervening portion of the length of the catheter between the at least two navigated electrode elements. Further, one or more virtually navigable electrode elements may be affixed to the length of the catheter near one of the navigated electrode elements but outside of the intervening portion.

In another embodiment of the method, the catheter is steerable into one of a plurality of configurations with the length of the catheter taking the form of a shape definable by the location data of the at least two navigated electrode elements. The location data for the one or more virtually navigable electrode elements is then determined as a function of the defined shape and data representative of a displacement of the one or more virtually navigable electrode elements relative to a selected navigated electrode element of the at least two navigated electrode elements. In this embodiment of the method, the determination of the location of the virtually navigable electrode elements may include calculating parameters of a helix that defines an intervening section of the length of the catheter lying between the at least two navigated electrode elements as function of orientation data and positional coordinate data of the at least two navigated electrode elements and determining the positional coordinate data for the virtually navigable electrode elements using the helix defining the intervening section and the predetermined distance of the one or more virtually navigable electrode elements from at least one of the at least two navigated electrode elements.

A system for navigating a catheter within a navigational domain in accordance with the present invention is also described. The system includes a catheter having a plurality of locatable electrode elements distributed along and affixed to a length of the catheter. The plurality of locatable electrode elements includes at least two navigated electrode elements and one or more virtually navigable electrode elements located along or near an intervening portion of the length between the at least two navigated electrode elements. The system further includes one or more transmitters to project magnetic fields into the navigational domain sufficient to induce signal values within the at least two navigated electrode elements representative of the location of the at least two navigated electrode elements within the navigational domain. A controller generates location data from the induced signal values for the at least two navigated electrode elements and determines location data for the one or more virtually navigable electrode elements as a function of the location data for the at least two navigated electrode elements.

BRIEF DESCRIPTION OF THE DRAWINGS

FIG. 11A is a top view of the catheter. FIG. 11B is a detail top view of two coils at the tip of the catheter. FIG. 11C is a view of the catheter after being steered into a shape, i.e., a two dimensional or three dimensional shape.

FIG. 14A is a side view of the catheter. FIG. 14B is a diagrammatic planar view illustratively showing the various typical locations of the multiple electrodes of the catheter when the catheter is flattened against a structure into a single plane. FIG. 14C is a detailed view of the catheter when flattened into an ideal position taken from the center of the diagram of FIG. 14B.

DETAILED DESCRIPTION OF THE EMBODIMENTS

Figure 2:
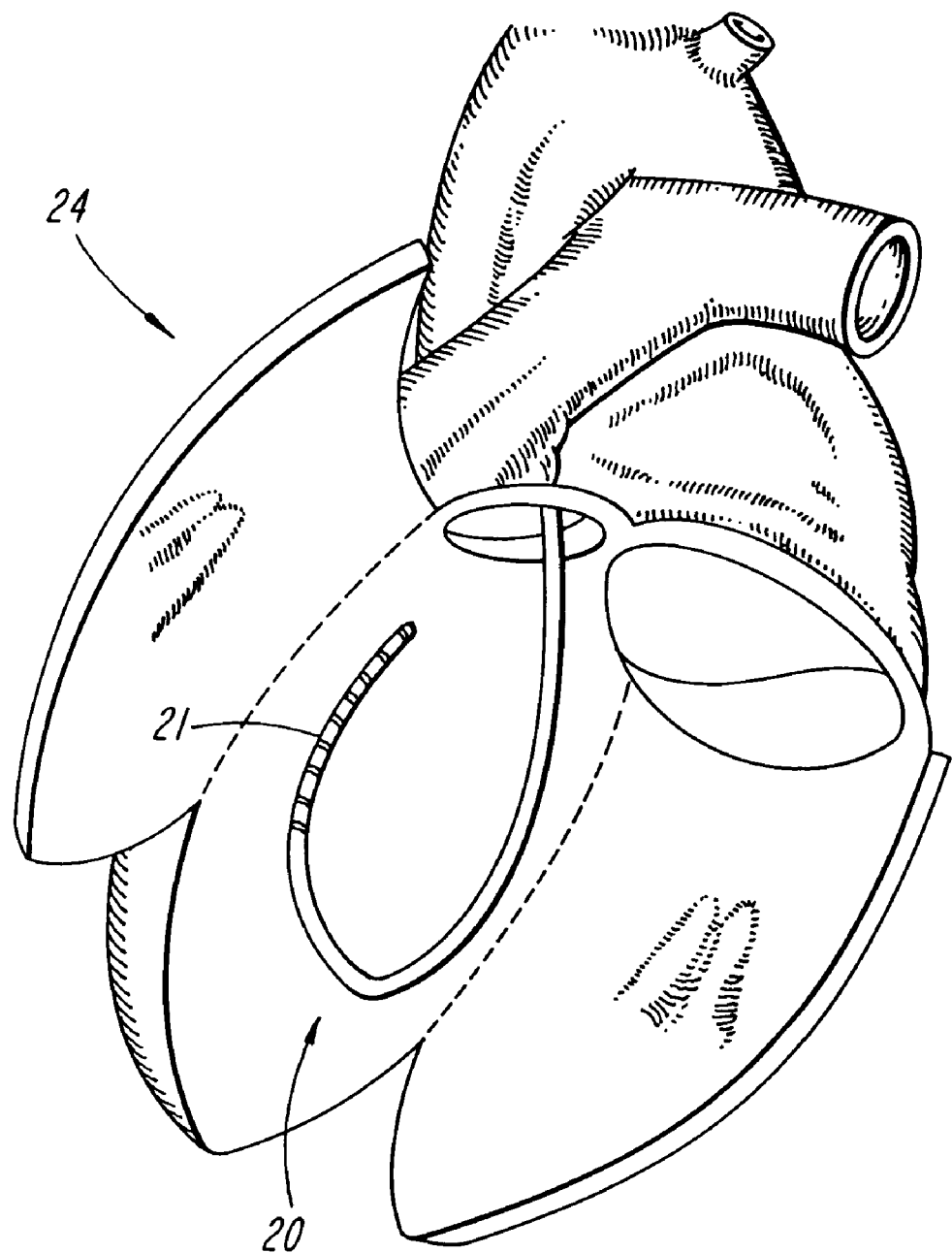
FIG. 2 is an illustrative view of a body organ having a multiple electrode catheter according to the present invention being navigated in the organ's internal space.

The present invention is directed to a method and system for navigation of a multiple electrode catheter within a navigational domain. For example, as shown in FIG. 2, the present invention may be utilized for navigating a steerable multiple electrode catheter 20 within a chamber of a heart 24 of a patient undergoing an electrophysiology procedure. The present invention utilizes location data for two or more navigated electrode elements positioned along a length of the catheter to determine the location of other electrode elements positioned in intervening sections of the length of the catheter lying between the two or more navigated electrode elements or other electrode elements positioned near but outside of the intervening sections. This determination of location of such other electrode elements is referred to herein as "virtual" navigation.

The multiple electrode catheter navigation system 10 and navigational method, including a virtual navigation process, according to the present invention shall be described generally with reference to FIGS. 1–8. Thereafter, several other specific embodiments of systems and methods according to the present invention shall be described with reference to FIGS. 9–15.

Figure 1:
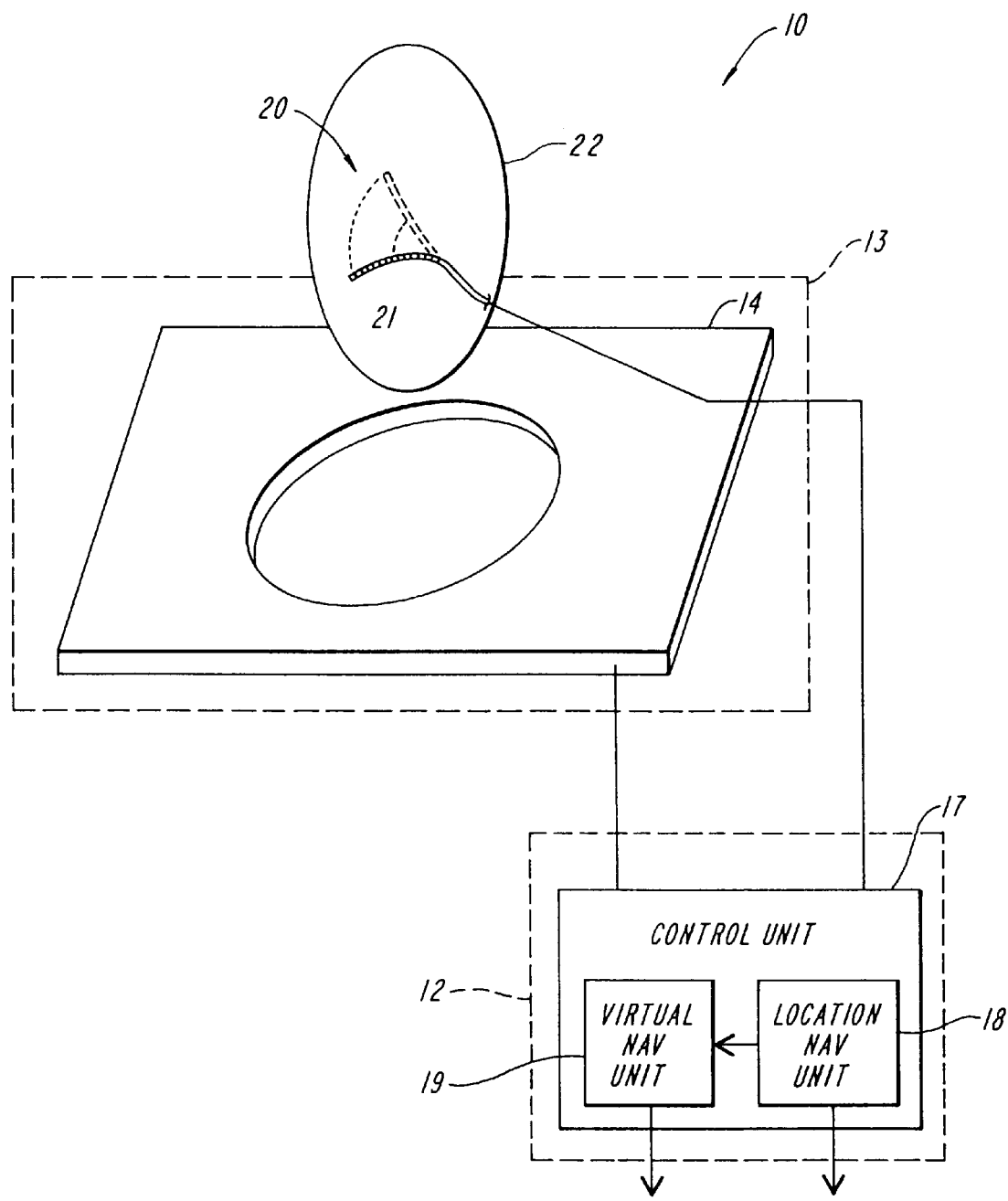
FIG. 1 is a diagrammatic view of a generalized navigation system according to the present invention.

As shown in FIG. 1, the multiple electrode catheter navigation system 10 according to the present invention includes a navigation apparatus 13, controllable by control unit 17, for use with steerable multiple electrode catheter 20 to provide control unit 17 with information regarding the location of the catheter within a navigational domain 22. For example, the navigational domain 22 may be a chamber of a heart 24, as shown in FIG. 2.

Figure 3A:
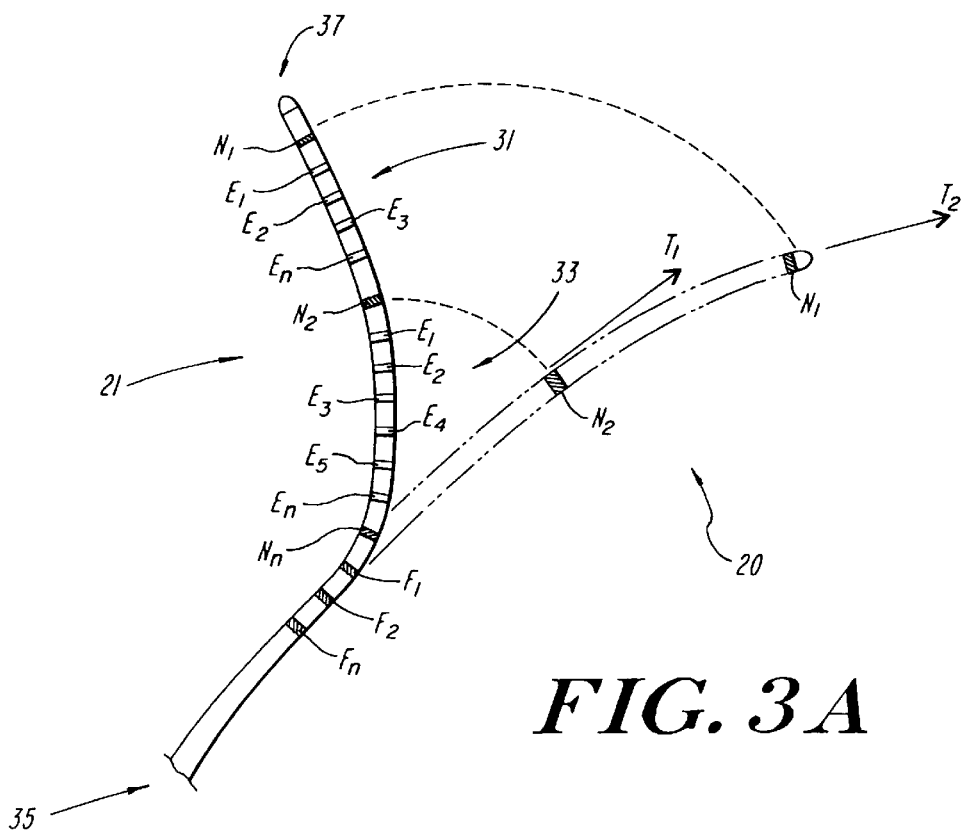
FIG. 3A is a more detailed view of the multiple electrode catheter of FIG. 1.

The generalized multiple electrode catheter 20, as shown in detail in FIG. 3A includes navigated electrode elements $N_1-N_n$. The navigated electrode elements $N_1-N_n$ are distributed along an end length 21 of the catheter 20. Between pairs of the navigated electrode elements $N_1-N_n$ are positioned virtually navigable electrode elements $E_1-E_n$. The virtually navigable electrode elements $E_1-E_n$ are preferably distributed in intervening sections 31, 33 of the end length 21 of the catheter 20 between pairs of the navigated electrode elements $N_1-N_n$. However, virtually navigable electrode elements may be positioned nearby a navigated electrode element yet lie outside the intervening sections 31, 33. For example, navigable electrode elements $F_1-F_n$ lying outside of the intervening section 31, 33 towards the proximal end of the catheter 35 opposite the distal end 37 are virtually navigable by the navigation system 10 if the electrode elements are positioned nearby a navigated electrode element $N_1-N_n$.

The control unit 17 includes location navigation unit 18 and virtual location navigation unit 19 which are implemented with processor, software and/or hardware capabilities. The control unit 17, including location navigation unit 18, is suitable for generating location data for each of the navigated electrode elements $N_1-N_n$ distributed along catheter end length 21. The virtual navigational unit 19 is suitable for generating location data of virtually navigable electrode elements $E_1-E_n$, $F_1-F_n$ based on location data generated by the location navigation unit 18.

As used herein, "navigated," such as for example, navigated electrode elements, refers to the generation of location data for such electrode element with any suitable location detection method, such as for example, the use of electromagnetic fields inducing signals in electrically conductive coils or other magnetic sensors, acoustic fields, etc., using the electrode element themselves or components directly affixed to such elements, such as colocated components. Further, as used herein, "virtually navigable," such is virtually navigable electrode elements, refers to the generation of location data using location data of other electrode elements or components associated therewith, e.g., location data of navigated electrode elements, as opposed to generating the location data with a location detection method that uses the electrode element itself or a component directly affixed or associated with the electrode element.

Control unit 17, including location navigation unit 18, may be any suitable apparatus for functioning in conjunction with catheter 20 and navigation apparatus 13 to generate location data with respect to the navigated electrode elements $N_1-N_n$. The catheter 20 may be any catheter having a steerable length containing multiple electrode elements, e.g., a length steerable into a two or three dimensional shape from an initial baseline shape. For example, the catheter may include an end length have an initial baseline shape that is a straight line, such as described with respect to FIG. 11A–11C. Further, for example, the catheter may have an end length having an initial baseline shape that is a tapered spring-like shape (FIGS. 14A–14C), or the length having the navigated and virtually navigable electrode elements distributed therealong may take any other form which is steerable from an initial baseline shape into a two or three dimensional shape.

The multiple navigated electrode elements distributed along the end length 21 of catheter 20, e.g., navigated electrode elements $N_1-N_n$, may be any electrode element which in combination with the navigation apparatus 13 is suitable for providing information, signals, data, etc. for determining navigational location information regarding the location of the navigated electrode element, within the navigational domain 22. For example, the navigated electrode elements may be electrically conductive coils in which signals are induced by surrounding transmitted electromagnetic fields projected into the navigational domain using transmit coils of the navigation apparatus, such as described in U.S. Pat. No. 5,592,939 to Martinelli, entitled "Method and System for Navigating a Catheter Probe," entirely incorporated herein by reference. Such navigated electrode elements may be RF transmit coils utilized with receivers of a navigation apparatus 13 for determining location of the transmit coils, such as described in U.S. Pat. No. 5,211,165 to Dumoulin et al. entitled "Tracking System to Follow the Position and Orientation of a Device with Radiofrequency Field Gradients," entirely incorporated herein by reference. Further, the electrode elements may include a metal band, or a metal band having an associated or colocated coil, or any other configuration which allows for the direct navigation of the electrode element by the determination of location data for such an electrode element using the electrode element itself in the location determination process or an associated or colocated component, such as, for example, a colocated coil. Preferably, coils are used as they allow greater flexibility of the catheter, i.e., bending, and therefore, can be of a greater length than a band.

It should be readily apparent to one skilled in the art that any number of different navigated electrode elements $N_1-N_n$ and navigation apparatus 13 may be used in combination to provide signals to control unit 17 for determination of the location of the navigated electrode elements $N_1-N_n$ using a compatible location navigation unit 18. The only necessary requirement of the process, system, or apparatus for generating location data for the navigated electrode elements $N_1-N_n$ is that the output of the location navigation unit 18 be capable of generating location data with respect to the navigated electrode elements $N_1-N_n$ that is usable by the virtual navigation unit 19 in generating location data for the virtually navigable electrode elements $E_1-E_n$, $F_1-F_n$ (e.g., generation of orientation data and positional coordinate data for the navigated electrode elements $N_1-N_n$ within the navigational domain 22).

The virtually navigable electrode elements $E_1-E_n$, $F_1-F_n$ (hereinafter, in most circumstance referred to as electrode elements $E_1-E_n$) for which location information is generated using location data of the navigated electrode elements $N_1$–$N_n$ may be the same type of electrode elements as the $N_1$–$N_n$ electrode elements or may be different from such electrode element types. Such virtually navigable electrode elements need not have the ability to provide information, signals, data, etc. for determining navigational location of the electrode element within a navigational domain because the location of such electrode elements is determined by virtual navigation. As such, the virtually navigable electrode elements can be one wire connected electrode elements (such as for sensing electrograms) as compared to the navigated electrode elements which are two wire connected elements (such as for use in sensing electromagnetic fields).

As shown in FIG. 1, the steerable catheter 20 is steerable within the navigational domain 22. The volume of the navigational domain 22 is determined by the domain in which the location of the navigated electrode elements $N_1$–$N_1$ can be accurately determined with use of the navigated electrode elements $N_1$–$N_n$, the navigation apparatus 13, and control unit 17. Under surgical operating conditions, the navigational domain will incorporate an anatomical region of the patient where surgical viewing or investigation is desired (e.g., a diseased area of tissue, a vessel, or an organ). In the case of electrophysiology, the navigational domain incorporates the entire heart.

The virtual navigation unit 19 of control unit 17 determines location data for the virtually navigable electrode elements $E_1$–$E_n$ as a function of the location data for the navigated electrode elements $N_1$–$N_n$. Generally, when the catheter 20 is positioned in the navigational domain 22 (e.g., such as in an initial baseline configuration, a steered two or three dimensional configuration within an open and free volume unaffected by external forces (e.g., forces exerted by chamber walls, vessels, etc.), or a steered two or three dimensional configuration within the navigational domain affected by such external forces), the location data for virtually navigable electrode elements $E_1$–$E_n$ distributed along length 21 of catheter 20 is determined using memory of the control unit 17 containing sets of displacement coordinates for the virtually navigable electrode elements. Each set of displacement coordinates represents experimentally determined deviations of the virtually navigable electrode elements $E_1$–$E_n$ from a selected one of the navigated electrode elements $N_1$–$N_n$ when the navigated electrode elements $N_1$–$N_n$ are at a particular location relative to one another. The experimental determination shall be described further below, but generally, the experimentally predetermined relationship between the virtually navigable electrode elements $E_1$–$E_n$ and the navigated electrode elements $N_1$–$N_n$ is based on the mechanical characterization of the catheter, i.e., the stiffness and flexing characteristics. These mechanical characteristics "lock" any set of $N_1$–$N_n$ coordinates to a corresponding set of $E_1$–$E_n$ coordinates. Therefore, when the catheter 20 is moved to multiple positions within the navigational domain 22, the location of the virtually navigable electrode elements $E_1$–$E_n$ at a particular location can be determined by selecting a corresponding locked set of displacement coordinates corresponding to the known locations of the navigated electrode elements $N_1$–$N_n$. The location data for the virtually navigable electrode elements $E_1$–$E_n$ is then generated based on the location of the selected navigated electrode elements and the set of displacement coordinates, e.g., adding the displacement coordinates to the positional coordinates of the selected navigated electrode element.

One skilled in the art will recognize that the navigated and virtually navigable electrode elements according to the present invention can be used for multiple purposes, in addition to navigating the catheter. Such electrode elements may be used for mapping, ablation, etc. as is generally represented by the optional application specific system 12. The application specific system 12 provides the specific control over the use of the electrode elements for such functions or specific applications. For example, the application system 12 may be an ablation system controllable thereby for performance of ablation at particular locations on a heart wall. Any such application system may benefit from the virtual navigation of locatable electrode elements in accordance with the present invention.

Further, and in general, the multiple electrode catheter navigation system 10 in accordance with the present invention shall be described with reference to FIGS. 1–8 wherein the navigated electrode elements $N_1$–$N_n$ are electrically conductive coils and navigation apparatus 13 includes a platform containing coils for projecting predetermined and prespecified electromagnetic fields into the navigational domain 22 such as those described in U.S. Pat. No. 5,592,939, entirely incorporated herein by reference. The location data is generated from electrical measurements of signals that are induced within sensing coils $N_1$–$N_n$ by the electromagnetic fields projected into the navigational domain. The electrical measurements of the induced signals provide sufficient information to control unit 17 for generation of location data for the navigated electrically conductive coils $N_1$–$N_n$.

Figure 4:
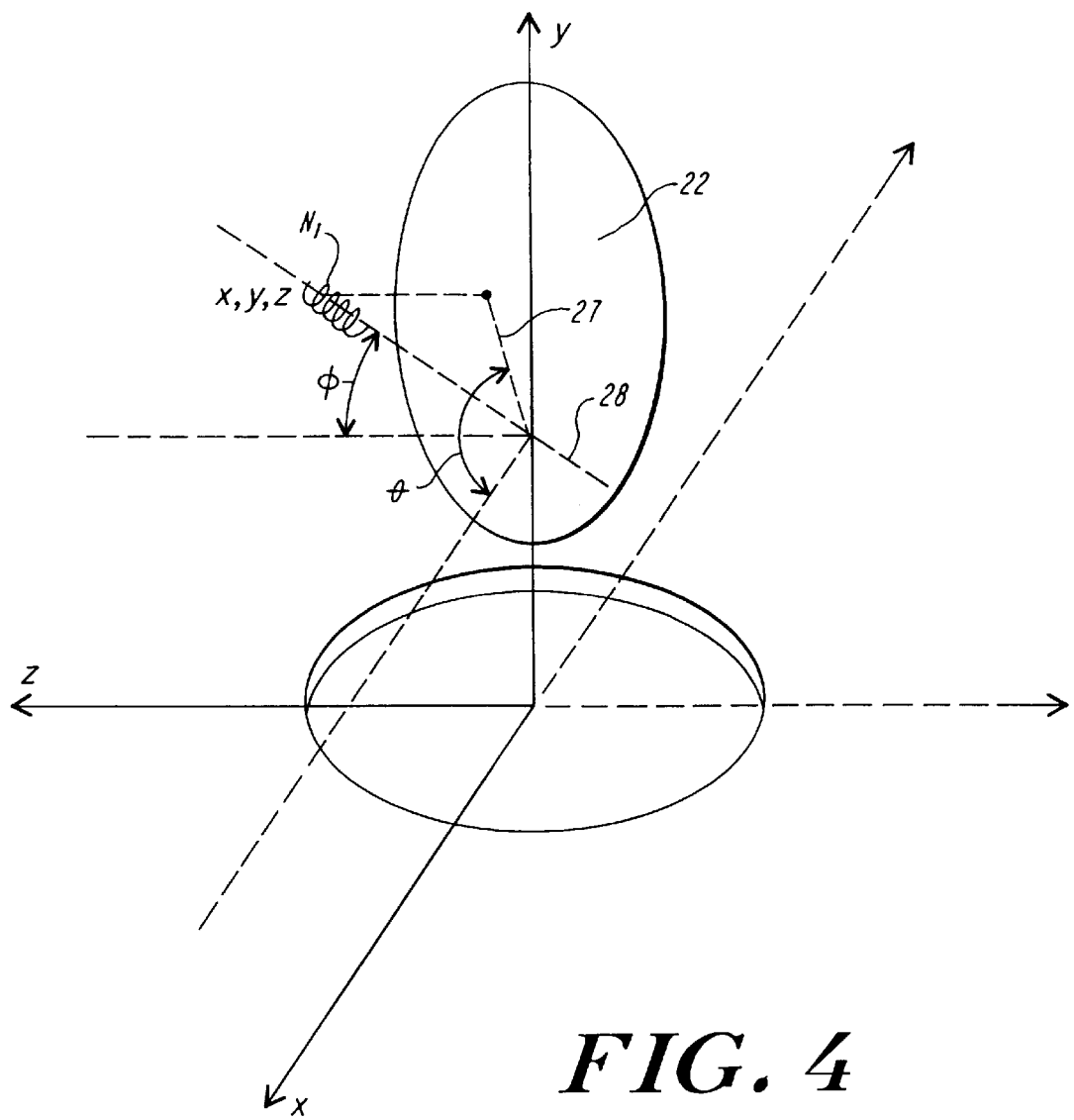
FIG. 4 is a diagrammatic view of an illustrative coil of the multiple electrode catheter of FIGS. 1–3 illustrating the position and orientation data required for navigation of a coil within a navigational domain.

As shown in FIG. 4, the location of one of such coils $N_n$ of a collection of coils $N_1$–$N_n$ affixed to the catheter 20 at the end length 21 which is navigated through navigational domain 22, e.g., an anatomical region of interest within the patient, is defined by angular orientation $(\theta,\phi)$ and positional coordinates $(x, y, z)$ The angular orientation is represented by an angle $\phi$ corresponding to the angle of departure from the z-axis and an angle $\theta$ corresponding to the angle between the x-axis and the projection 27 onto the x–y plane of the vector coincident with the longitudinal axis 28 of the coil $N_n$. Generally, for example, the coordinate system can be described as the z-axis coinciding with the longitudinal dimension extending from a patient's head to foot, the x-axis coincides with a lateral dimension across the patient's body, and the y-axis is perpendicular to the planar top of a surface such as the platform 14 (FIG. 1).

Figure 3B:
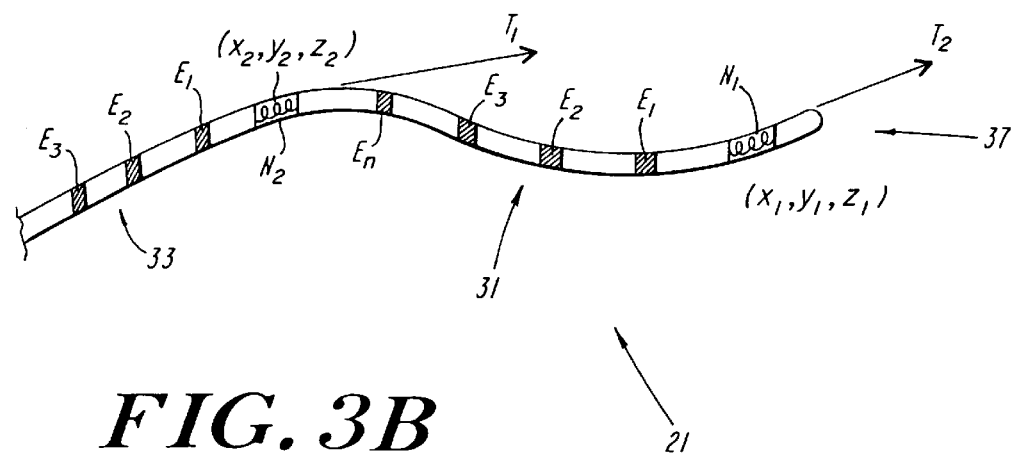
FIG. 3B is a detailed view of the multiple electrode catheter of FIG. 3A maneuvered, e.g., steered, into a different shape.

As discussed in U.S. Pat. No. 5,592,939, the angular orientation is determined from signals induced in the coil in response to a sequence of substantially uniform, unidirectional fields generated successively within the navigational domain 22. The uniform unidirectional fields refer to magnetic fields having a large magnetic field component in a specified axial dimension, i.e., the x, y, and z directions, and characterized by substantially uniform field values throughout the navigational domain. The positional coordinates are determined from signals induced in the coil in response to the gradient magnetic fields in the navigational domain. Such gradient magnetic fields refer to time-dependent magnetic fields having non-zero field components (i.e., components with a high spatial gradient) in two of the three axial dimensions for the coordinate system of interest (e.g., x, y, z system), and a substantially zero component in the remaining axial dimension. As shown in FIGS. 3A and 3B, the navigated coils each have positional coordinates $(x_n, y_n, z_n)$ associated therewith and a tangent vector $T_n$ associated therewith. The $T_n$ is defined by the angular orientation $(\theta, \phi)$ of the navigated coil.

As shown in FIG. 3A, the tangent vectors $T_1$, $T_2$ for the navigated coils $N_1$ and $N_2$ are such that the intervening section 31 can be defined by a helix, for example, if the catheter is being maneuvered in an open and free volume of the navigational space. FIG. 3B on the other hand, shows tangent vectors $T_1$, $T_2$ for the navigated coils $N_1$, and $N_2$ that are generally parallel to one another such as might arise if there is a force being transmitted into the catheter tip, i.e., distal end 37. In such a configuration, the shape is generally very complex and undefinable by any simple geometric shape. As will be apparent from the description herein, the location of virtually navigable electrode elements for configurations having intervening sections that are definable by geometric shapes, e.g., a helix (FIG. 3A), may be determined in a manner that is different than the process used for configurations that have a more complex shape (FIG. 3B).

Further, although the preferred methods of determining the location data ($\theta$, $\phi$, x, y, z) for the coils $N_1$–$N_n$ are as described above and in further detail in the U.S. Pat. No. 5,592,939, other methods of determining such location data are equally applicable. For example, if the navigated electrode element is a transmitting coil as opposed to a sensing coil, a different method of determining such location data for the navigated electrode element is used, e.g., a method wherein the navigation apparatus 13 includes receiver elements. It should be readily apparent that the present invention is in no manner limited to the method of determining location data for the navigated points as described or listed herein and that any suitable method of obtaining location data for the navigated electrode elements is acceptable.

Figure 5:
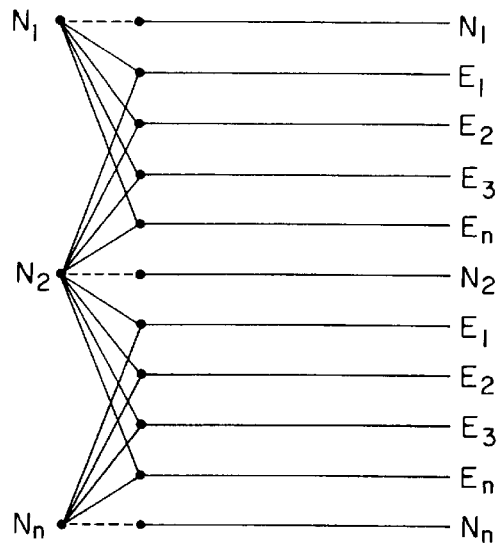
FIG. 5 is a diagram generally illustrating virtual navigation in accordance with th e present invention.
Figure 6:
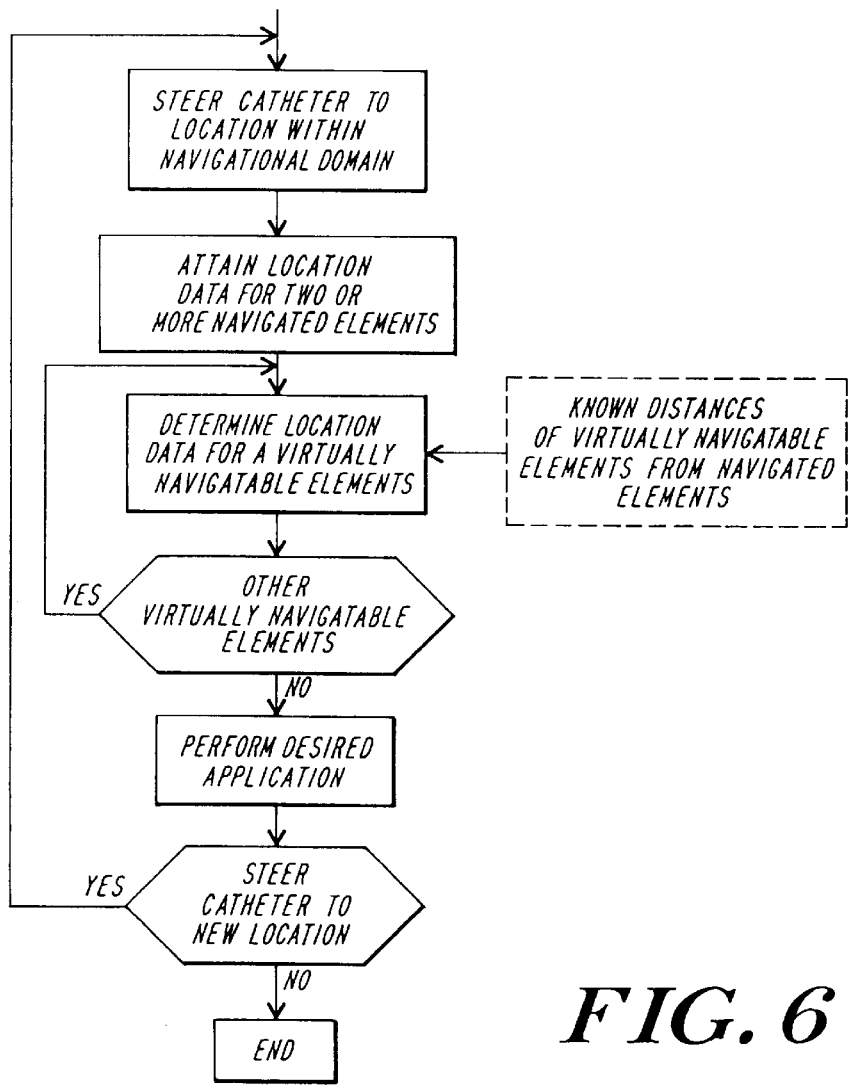
FIG. 6 is a flow diagram of a generalized navigation process using virtual navigation according to the present invention for navigating the illustrative multiple electrode catheter shown in FIGS. 1–3.

The method of navigating the multiple electrode catheter 20 is generally shown in FIGS. 5 and 6. As shown in the diagram of FIG. 5, the location of navigated electrode elements $N_1$ and $N_2$ are used to determine the locations for virtually navigable electrode elements $E_1$–$E_n$ distributed therebetween. Further, the location of another set of virtually navigable electrode elements $E_1$–$E_n$ are determined using the location data of navigated electrode elements $N_2$ and $N_n$.

As shown in the flow diagram of FIG. 6, the multiple electrode catheter 20 is steered to a location within the navigational domain 22. With the catheter 20 at this location and the end length 21 steered into a particular shape, location data for the navigated coils $N_1$–$N_n$ is attained by a method as described above. For example, as described in the method of U.S. Pat. No. 5,592,939, angular orientation data ($\theta_n$, $\phi_n$) and positional coordinate data ($x_n$, $y_n$, $z_n$) for the navigated coils $N_1$–$N_n$ are determined.

Thereafter, the location data for each of the virtually navigable coils $E_1$–$E_n$ is determined. The following description shall be limited to the determination of location data for one set of virtually navigable coils $E_1$–$E_n$ lying along the intervening section 31 of the length 21 of catheter 20, but a substantially similar process is equally applicable to the other sets of virtually navigable coils $E_1$–$E_n$ lying along other intervening sections, i.e., intervening sections 33, and virtually navigable coils $F_1$–$F_n$ positioned nearby a navigated coil $N_1$–$N_n$ but outside of an intervening section.

Figure 7:
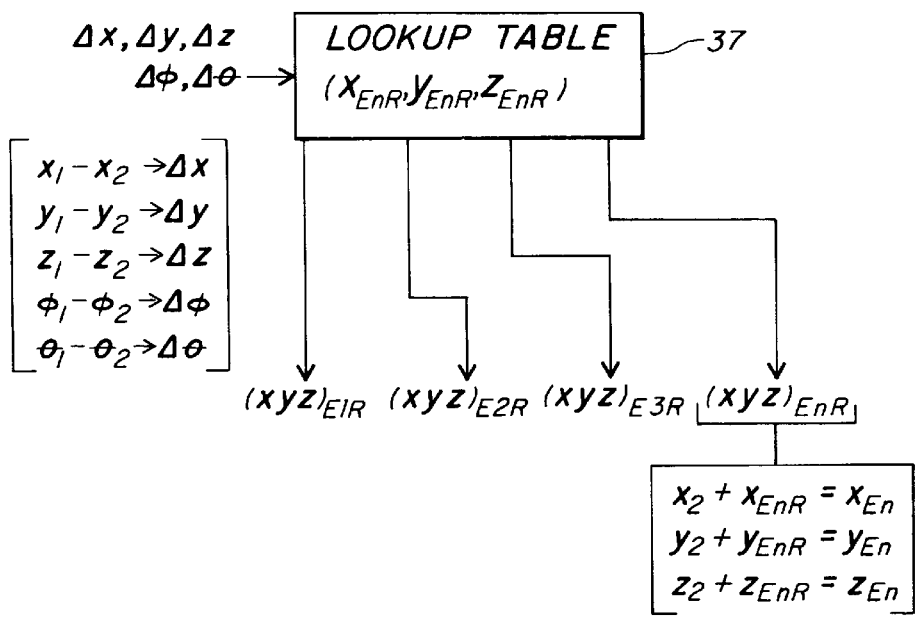
FIG. 7 is a block diagram showing the inputs and outputs of a lookup table used in the navigation process of FIG. 6 for navigating the illustrative multiple electrode catheter.

The virtual navigation unit 19 includes an empirical lookup table 37 as shown in FIG. 7 which is utilized to determine the location data for the virtually navigable coils $E_1$–$E_n$ distributed along intervening section 31 of length 21 of catheter 20 using the location data of navigated coils $N_1$ and $N_2$. The lookup table 37, or any other suitable addressable memory apparatus operable for communication with the control unit 17, is used for storing sets of displacement coordinates for the virtually navigable electrode elements $E_1$–$E_n$. Each set of displacement coordinates represents the general deviation, determined experimentally, of the virtually navigable coils $E_1$–$E_n$ from one of the navigated coils $N_1$ and $N_2$ when the navigated coils $N_1$ and $N_2$ are at a particular location relative to one another when the end length 21 of the catheter 20 is in or has been steered into a particular shape which deviates from a baseline shape, e.g., a straight line baseline shape.

Figure 8:
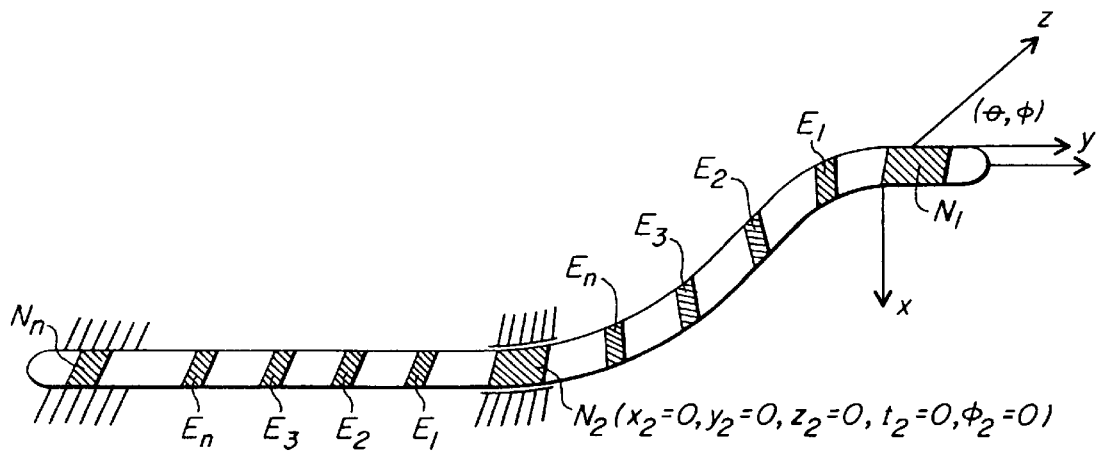
FIG. 8 is an illustrative diagram of the multiple electrode catheter shown in FIGS. 1–3 as used for providing experimental data for use in creating the lookup table of FIG. 7.

FIG. 8 shows an illustrative experimental setup for determining the sets of displacement coordinates for the lookup table 37. As shown in FIG. 8, navigated coil $N_2$ is clamped at a position (x=0, y=0, z=0, $\theta$=0, $\phi$=0). The navigated coil $N_1$ is placed at a sequence of locations and angles to encompass all practical positions the navigated coil $N_1$ may be steered to relative to $N_2$. At each of such positions associated with a particular location of $N_1$ relative to the location of $N_2$, the positional displacement coordinates ($x_{EnR}$, $y_{EnR}$, $z_{EnR}$) for the virtually navigable coils $E_1$–$E_n$ are measured and recorded into the lookup table 37 in a manner such that they are addressable by a delta location ($\Delta x$, $\Delta y$, $\Delta z$, $\Delta\theta$, $\Delta\phi$). The delta location is the difference value of each angular measurement ($\theta_n$, $\phi_n$) and positional coordinate data ($x_n$, $y_n$, $z_n$) of $N_1$ relative to $N_2$. In the test setup, with the position of $N_2$ clamped at and equal to a location of (x=0, y=0, z=0, $\theta$=0, $\phi$=0), then the delta location ($\Delta x$, $\Delta y$, $\Delta z$, $\Delta\theta$, $\Delta\phi$) of $N_1$ relative to $N_2$ is equal to the location of $N_1$ or ($\theta_1$, $\phi_1$, $x_1$, $y_1$, $z_1$).

Then, when the catheter 20 is moved to one of the multiple practical positions within the navigational domain 22, the location of the virtually navigable coils $E_1$–$E_n$ can be determined by comparing the location data for t he two navigated coils $N_1$, $N_2$. The difference between the angular orientation and positional coordinates of $N_1$($\theta_1$, $\phi_1$, $x_1$, $y_1$, $z_1$) and the angular orientation and positional coordinates of $N_2$($\theta_2$, $\phi_2$, $x_2$, $y_2$, $z_2$) result in the delta location ($\Delta x$, $\Delta y$, $\Delta z$, $\Delta\theta$, $\Delta\phi$) for that particular position of the catheter within the navigational domain. The delta location is then used to address the lookup table, or otherwise select from a memory, a set of displacement coordinates corresponding to this particular delta location determined using the test setup.

The lookup table will have a finite number of table elements corresponding to a discrete finite set of inputs that encompass all practical positions of $N_1$ relative to $N_2$. The lookup table may include interpolation capability when an input falls between such discrete inputs.

The set of displacement coordinates may be provided from the lookup table in serial or parallel form. As shown in FIG. 7, the set of displacement coordinates is provided in parallel form, i.e., in multiple channels, with each channel including the displacement coordinates applicable to one of the virtually navigable coils. The displacement coordinates ($x_{EnR}$, $y_{EnR}$, $z_{EnR}$) for each of the virtually navigable coils are then added to the positional coordinates of $N_2$($x_2$, $y_2$, $z_2$) resulting in the virtual determination of the location of the virtually navigable coils. For example, $x_{E1R}$ is added to $x_2$ to obtain the x coordinate $x_{E1}$, and the y and z coordinates are added in the same manner. Likewise the location of the other virtually navigable coils are determined in substantially the same manner. It should be readily apparent that the lookup technique may be implemented in various manners and that the above process is for illustration only.

As further shown in FIG. 6, the determination of locations for virtually navigable coils is performed until the location of all desired coils is known. Optionally thereafter, with the known location of both the navigated and navigable coils, various functions can be performed such as the taking of electrograms, ablation techniques, etc. at the particular locations. Further, after any desired functions are performed at the determined locations, the catheter may be steered to a new shape or position within the navigational domain 22 and the process repeated until an end position for the catheter is attained.

Preferably., the location of the virtually navigable coils are determined using the lookup table process as described above, particularly when the catheter can be steered, or has forces applied thereto such that the shape of the intervening section between the navigated coils is somewhat complex, i.e., not easily definable by a geometric shape. However, when the length 21 of the catheter is in free and open space (e.g., blood filled space), without external forces being applied thereto resulting in such a complex shape, a sufficiently short catheter section, e.g., the intervening section 31 of catheter 20 lying between two navigated electrode elements $N_1$ and $N_2$, takes the form of a geometric shape that is definable using location data at the ends of the intervening section. For example, as shown in the specific illustration of FIG. 9A, when the end length 21 is steered into a three dimensional shape, the intervening section 31 of the catheter 20 takes the form of a helix as shown by the extended dotted helix 51 having axis 53 therethrough.

The helix 51 corresponding to a catheter intervening section 31 lying between the two navigated electrode elements $N_1$ and $N_2$ can be defined using the location data of the navigated electrode elements $N_1$ and $N_2$. The defined helix 51 can then be used in conjunction with the known distances (as represented by the dashed block of the flow diagram of FIG. 6) between the navigated electrode elements $N_1$ and $N_2$ and the virtually navigable electrode elements $E_1$–$E_n$, to determine the locations of the virtually navigable electrode elements $E_1$–$E_n$ within the navigational domain 22. After attaining the location data for the navigated electrode elements $N_1$ and $N_2$, the location data for each virtually navigable electrode element $E_1$–$E_n$ is determined as a function of the location data for the navigated electrode s elements $N_1$ and $N_2$ and known distances of the virtually navigable electrode elements $E_1$–$E_n$ from at least one of the navigated electrode elements $N_1$ and $N_2$.

The description with respect to the determination of locations for virtually navigable electrode elements based on location data of navigated electrode elements, defining a geometric shape, e.g., a helix, is limited to the navigated electrode elements $N_1$, $N_2$ and the virtually navigable electrode elements $E_1$–$E_n$ distributed therebetween for simplicity purposes. However, it should be readily apparent that the same location determination process may be used for additional intervening sections between navigated electrode elements and/or for virtually navigable electrode elements lying nearby such navigated electrode elements but outside the intervening section.

As shown in FIGS. 9A–9C and 10, the location data of navigated electrode elements $N_1$, $N_2$ provided from the location navigation unit 18 as previously described, allows a geometric shape to be defined for intervening section 31 of the catheter 20 leading to the solution of location data for virtually navigable electrode elements $E_1$–$E_n$ distributed along the intervening section 31. Further, the geometric shape definable for intervening section 31 of the catheter 20 can be extended towards the proximal end 35 of the catheter 20 to further provide solution for location data of one or more navigable coils distributed along the end length 21 but outside of the intervening sections 31.

Figure 9A:
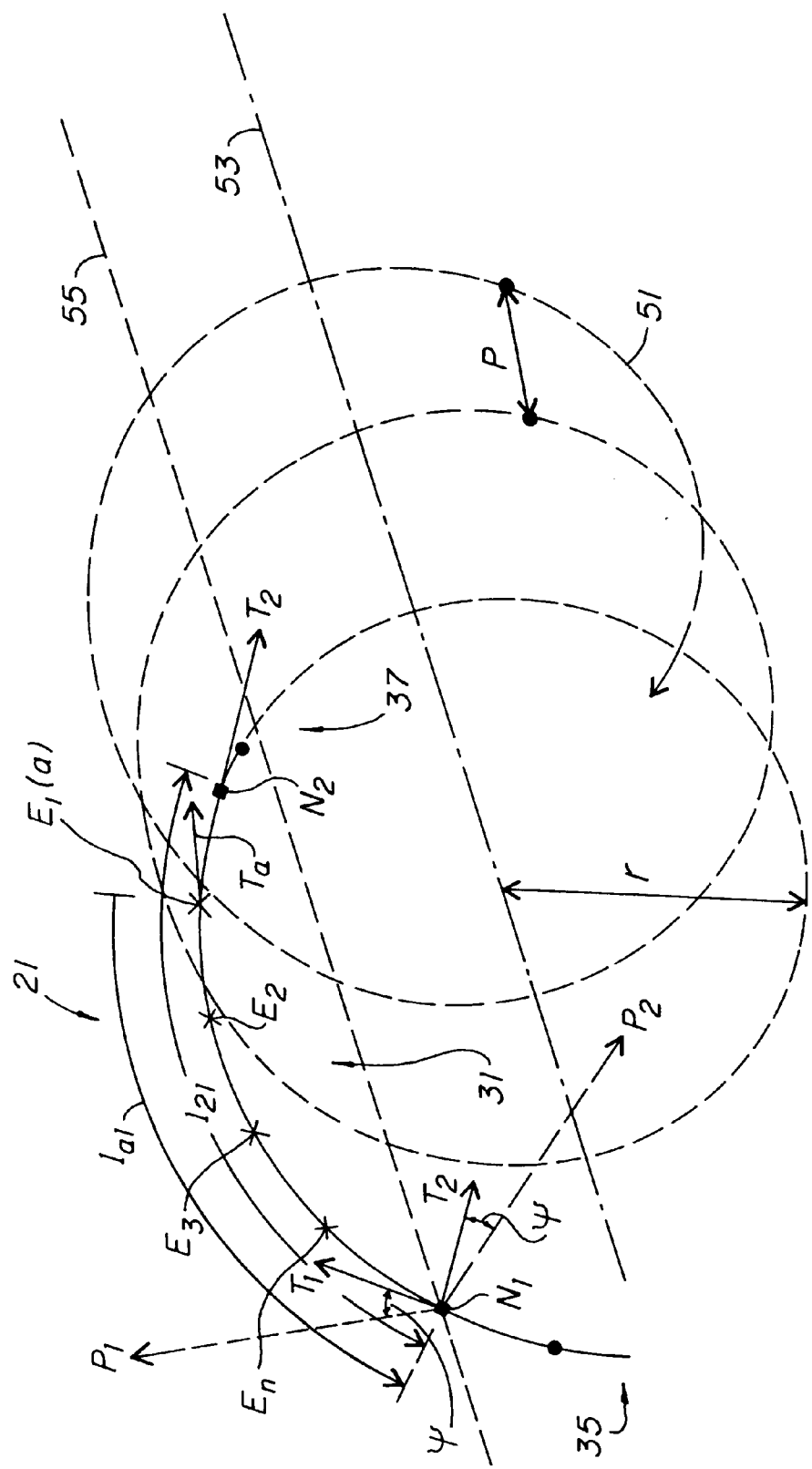
FIGS. 9A–9C are diagrammatic illustrations for use in describing the determination of location data for virtually navigable electrodes of the multiple electrode catheter of FIGS. 1–3 including a projected helix associated with the catheter shape.
Figure 9B:
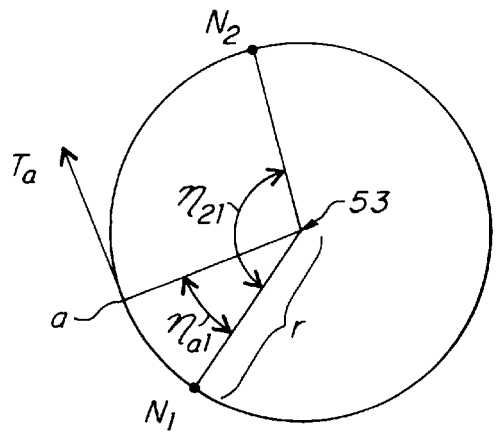
Figure 9C:
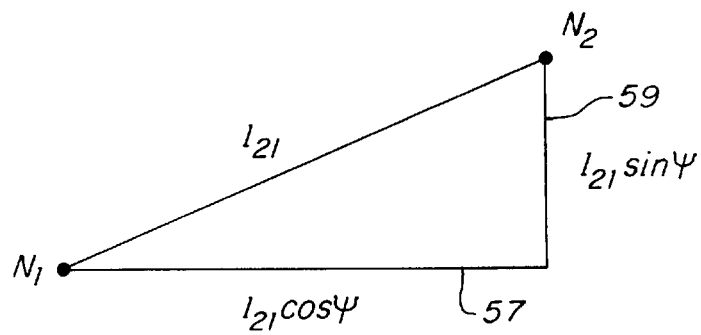

When the intervening section 31 is in free and open space without external forces applied thereto, the section 31 generally takes the form of a section of a definable helix 51 (FIG. 9A) which shows the navigated electrode elements $N_1$ and $N_2$, the tangent unit vectors at these elements $T_1$ and $T_2$, as well as various virtually navigable electrode elements $E_1$–$E_n$. The following description of determining location for the virtually navigable electrode elements $E_1$–$E_n$ shall be limited to the determination of the location of electrode element $E_1$ (herein after referred to as point "a." The helix lengths $l_{21}$ (i.e., the distance along the catheter from $N_1$ to $N_2$) and $1_{a1}$ (i.e., the distance along the catheter from $N_1$ to point "a") are also shown and are known values based on the construction of the catheter. A dotted line 55 parallel to the axis 53 of the helix 51 is drawn through $N_1$ as is a copy of the vector $T_2$. The dotted lines labeled $p_1$ and $p_2$ are perpendicular to the axis 53 and are in a plane formed by the axis 53 and $T_1$ and $T_2$ respectively. Both $T_1$ to $T_2$ have the same angle Q to these lines $p_1$ and $p_2$, respectively. FIG. 9B shows the same helix 51 as viewed along the axis 53. The relative azimuthal rotation of points $N_2$ and "a" about axis 53 is shown as $0_{21}$ and $0_{a1}$ in FIG. 9B, respectively, and further FIG. 9B shows tangent vector $T_a$. FIG. 9C shows the helix "unrolled" between $N_1$ to $N_2$.

Navigated vectors $R_1$ and $R_2$ are known from the navigation measurements and defined as follows:

$$\text{Equations (1) and (2):} \quad \begin{aligned} \hat{R}_1 &= x_1\hat{x} + y_1\hat{y} + z_1\hat{z} \\ \hat{R}_2 &= x_2\hat{x} + y_2\hat{y} + z_2\hat{z} \end{aligned}$$

Further, navigated vectors $T_2$, $T_2$ are known from navigation measurements. Only the components of $T_1$ and $T_2$ that are perpendicular to the axis 53 contribute to their cross product given in Equation (3). The horizontal line 57 in FIG. 9C corresponds to the azimuthal rotation arc length $0_{21}$ as shown in Equation (4). The normalized product $\vec{T}_2 \times \vec{T}_1$ is parallel to the axis 53 and hence when dotted with $\vec{R}_2 - \vec{R}_1$ gives the displacement along the axis 53 and corresponds to the vertical line 59 of FIG. 9C, as shown in Equation (5).

$$\left. \begin{aligned} &\text{Equation (3) } |T_2^\varpi \times T_1^\varpi| = (\cos\psi)\sin\eta_{21} \\ &\text{Equation (4) } l_{21}\cos\psi = r\eta_{21} \\ &\text{Equation (5) } \frac{(T_2^\varpi \times T_1^\varpi)\cdot(R_2^\varpi \times R_1^\varpi)}{|T_2^\varpi \times T_1^\varpi|} = l_{21}\sin\psi \end{aligned} \right\} \Rightarrow \begin{matrix} \eta_{21} \\ \psi \\ r \end{matrix}$$

where $\vec{T}_1, \vec{T}_2, \vec{R}_2, \vec{R}_1, l_{21}$ = known quantities

The solution of these three equations give the helix 51 defining parameters Q, $0_{21}$, and r. The above Equations are repeated in Equations (6) and (7) for the virtual navigable point "a" as follows:

$$\text{Equation (6)} \frac{l_{a1}\cos\psi}{r} = \eta_{a1}$$

$$\text{Equation (7)} T_a^\varpi \times T_1^\varpi = (T_2^\varpi \times T_1^\varpi)\sin\frac{\eta_{a1}}{\sin\eta_{21}}$$

These are then substituted in Equations (8) and (9) as given below to determine the parallel ($\Delta R_\parallel$) and perpendicular ($\Delta R\perp$) parts of $\vec{\Delta R}$ where $\Delta R = \Delta R_\parallel - \Delta R_\perp$. $R_a$ is the location of the virtually navigated point "a" ($x_a, y_a, z_a$) given in Equation 10 below.

Figure 10:
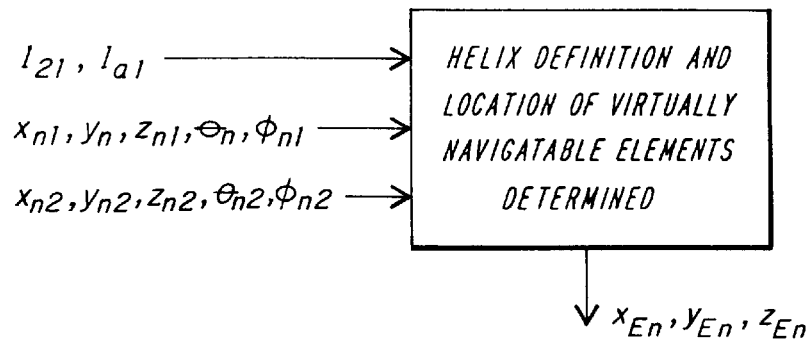
FIG. 10 is a block diagram showing the inputs and outputs of a virtual navigation unit used in addition to, or in the alternative to, at least portions of the navigation process of FIG. 6 for navigating the illustrative multiple electrode catheter shown in FIGS. 1–3.

Equation (8) $\frac{(T_a \times T_1) \times (R_a - R_1)}{|T_2 \times T_1|} = l_{aI}\sin\psi \Rightarrow \Delta R_\parallel$ Equation (9) $\frac{(T_a \times T_1) \cdot (R_a - R_1)}{|T_2 - T_1|} = 2\left(r\sin\left(\frac{\eta_{aI}}{2}\right)\right) \Rightarrow \Delta R_\perp$ Equation (10) $R_a = R_1 + \Delta R$ Therefore, as shown in the block diagram of FIG. 10, the helix definition and location of virtually navigable elements determined in accordance with the above Equations for ☐R yields the output of $x_{Ea}$, $y_{Ea}$, $z_{Ea}$.

One skilled in the art will recognize that the lookup process and the definable shape, e.g., helix, process can be used in combination or separately, depending upon the application being performed. For example, if navigation in a free and open space is being performed, then either process may be applicable. If forces are to be exerted onto the end length of the catheter resulting in complex shapes for the end length, then the lookup table process is more applicable. If navigation in free and open space and perpendicular external forces, e.g., contact with a wall, are going to be used in the application of the catheter, then both processes may be used. For example, if the catheter is being used in a heart chamber, the helix method of determining locations for the virtually navigable electrode elements may be used up until the time that external forces are applied to the catheter resulting in complex shapes for the end length. For illustration, the turning point for use of the lookup table method may be when an X-ray or "feel" of the catheter to the user indicates that external forces are being applied such that complex shapes not definable by a helix require the use of the lookup table process as opposed to a definable shape process.

Figure 11A:
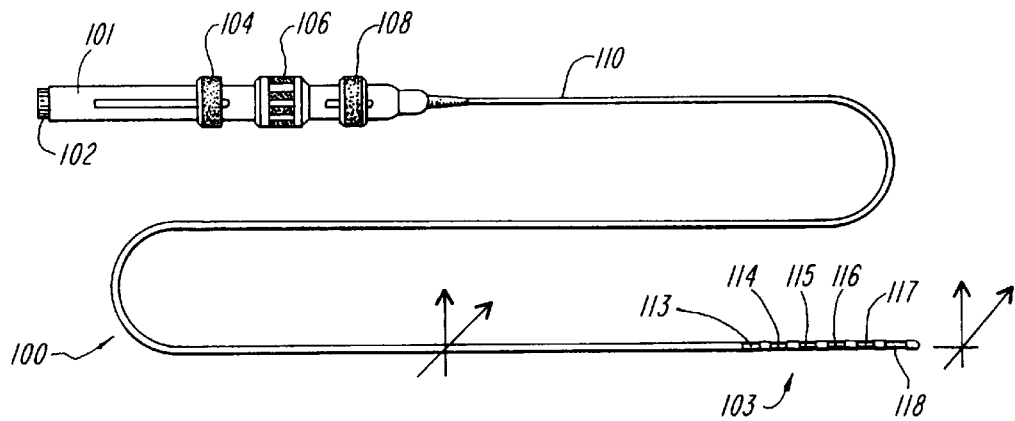
FIGS. 11A–11C are views of a particular multiple electrode catheter for use in a virtual navigation system according to the present invention.
Figure 11B:
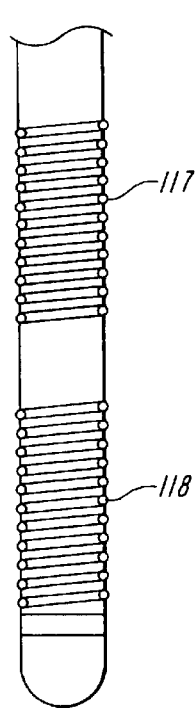
Figure 11C:
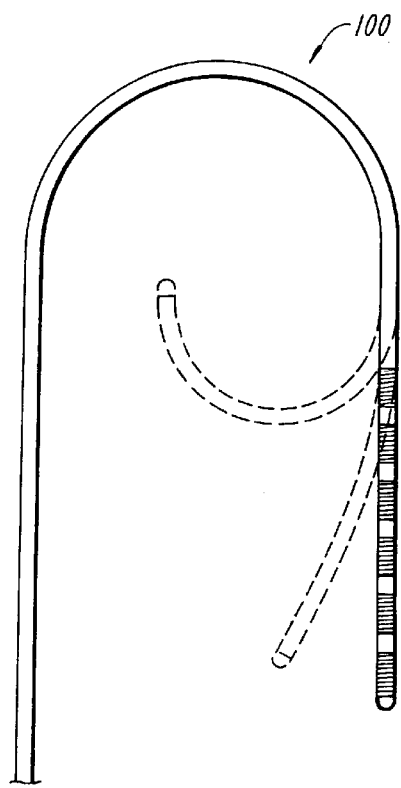

A particular embodiment of a catheter 100 is shown in FIGS. 11A–11C and shall be described along with the virtual navigation method of determining locations for virtually navigable coil electrodes distributed along a length thereof. FIG. 11A is a plan view of catheter 100. The catheter 100 includes handle 101 provided at the proximal end of the catheter 100. Handle 101 is provided with an electrical connector 102. Mounted to the handle are two sliding knobs 104 and 108, employed to longitudinally move separate tension wires within the catheter body 110. The structure and operation of knobs 104 and 108 and their associated tension wires are the same as the corresponding knobs and tension wires described in detail in U.S. Pat. No. 5,487,757, entirely incorporated herein by reference. Knob 106 is employed to rotate an internal, torqueing core wire, which extends within catheter body 110 to a point proximal to the electrodes 113–118; electrodes 113 and 118 being navigated electrodes and electrodes 114–117 being virtually navigable electrodes. The structure and operation of knob 106 and its associated internal wire also are the same as the corresponding knob and torqueing core wire described in U.S. Pat. No. 5,487,757. The tension wire coupled to knob 108 extends to the distal tip of the catheter, while the tension wire coupled to knob 104 extends only to a point just proximal to the illustrated electrodes. The combination of the two tension wires and the core wire allow for the catheter to be deflected into a multiplicity of configurations, e.g., two dimensional and three dimensional shapes, as illustrated below.

A detailed view of a couple of electrodes 117, 118 is shown in FIG. 11B. The electrodes 117, 118, and also the other electrodes shown in FIG. 11A, take the form of coil electrodes. The length of the coil electrodes may vary along with the separation distance between the electrodes. For example, such inter-electrode spacing may be about 1 millimeter to about 7 millimeters, with the electrode lengths, for example, being of about 5 millimeters to about 20 millimeters. Such dimensions are given for illustration only and in no manner are to be taken as limiting to the present invention. Each electrode is connected to connector 102 of the catheter 100 by an insulated wire as would be known to one skilled in the art. It should also be apparent that the electrodes may take one of various forms or configurations. For example, the electrodes may be plural ring electrodes or some other segmented electrode structures.

The deflection of the steerable end length 103 of the catheter 100 is shown in FIG. 11C. The end section 103 is steerable from its baseline straight configuration by manipulation of the tension wires previously described using knobs 104, 106, 108. As shown in FIG. 11C, the end length 103 can be manipulated into a variety of configurations, including nonplanar positions.

Figure 12:
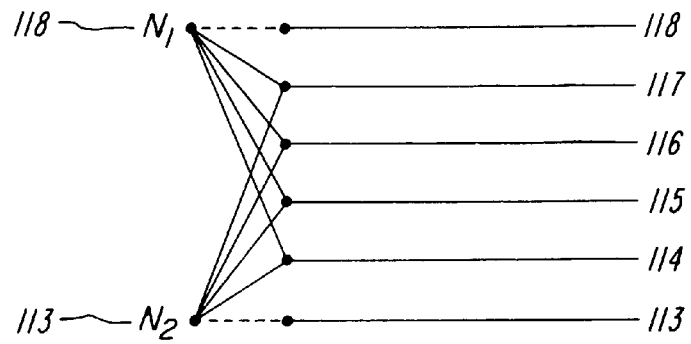
FIG. 12 is a diagram generally illustrating virtual navigation according to the present invention for the catheter of FIG. 11.

The determination of the location of coil electrodes 113–118 distributed along the end length 103 of the catheter 100 is diagrammatically represented in FIG. 12. The location of the virtually navigable coil electrodes 114–117 are shown as being determined as a function of the location of the navigated coil electrodes 113, 118.

Figure 13:
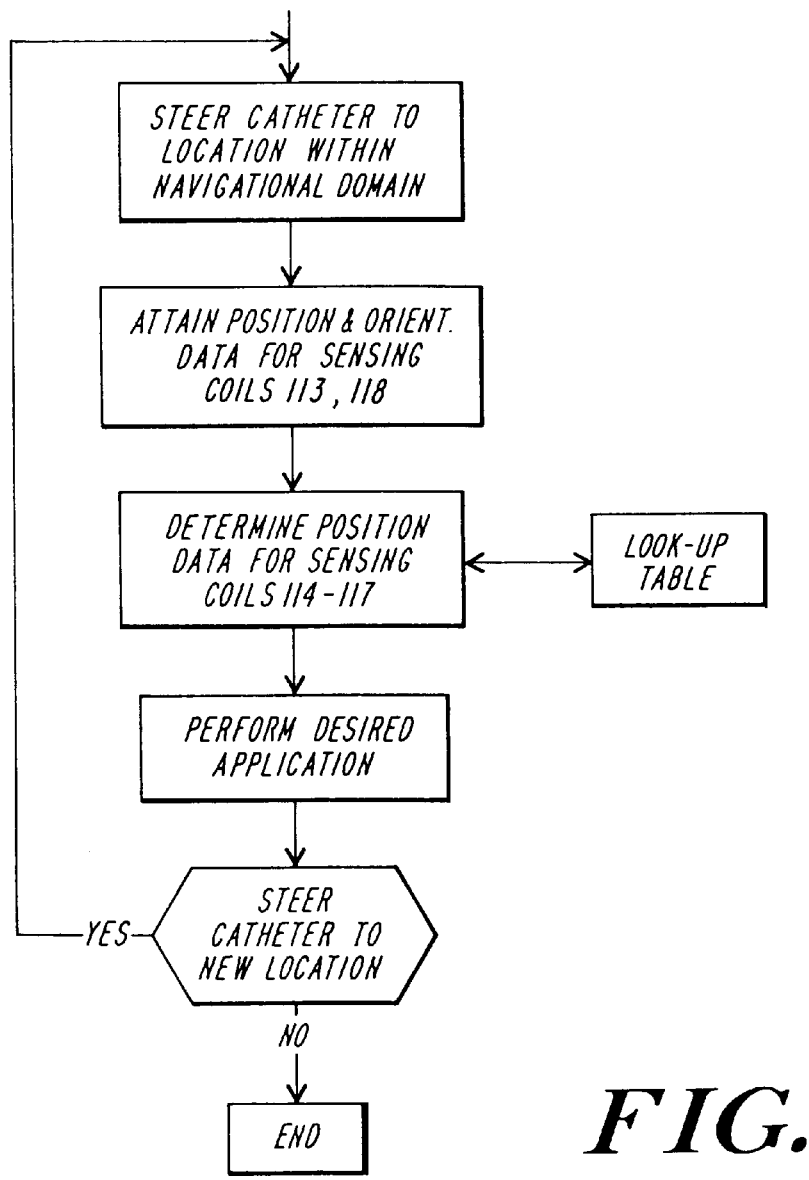
FIG. 13 is a flow diagram of a navigation process using virtual navigation according to the present invention for navigating the multiple electrode catheter shown in FIG. 11.

As described in the flow diagram of FIG. 13, which is substantially similar to the flow diagram of FIG. 6, the catheter 100 is positioned in a navigational domain and steered to a position or shape therein. The shape of the catheter, and particularly the end length 103, may be the same as or different from its baseline straight shape. With the catheter positioned in the navigational domain, e.g., a chamber of a heart, positional coordinates (x, y, z) and angular orientation data ((θ, φ) of the coil electrodes 113, 118 are attained by any known method, such as, for example, method s, as described above, e.g., methods of U.S. Pat. No. 5,592,939. Any known method of obtaining such positional coordinates (x, y, z) and angular orientation data ((θ,φ) of the navigated coil electrodes 113, 118 may be utilized and the present invention is in no manner limited to the methods as described herein.

After attaining the location data for the navigated coil electrodes 113, 118, the location data for each virtually navigable coil electrode 114–117 is determined as a function of the location data for the navigated coil electrodes 113, 118 using a lookup table created for the catheter 100 (e.g., a lookup table created with a test setup similar to that previously described), and location determination process substantially the same as, described with reference to FIGS. 6–8. It should be readily apparent that the helix method of determining locations for the virtually navigable coil electrodes may be used when suitable.

When the locations for all the coil electrodes 113–118 have been determined, then the catheter may be steered into a new location and the end length 103 may take another shape. Prior to the steering of the catheter 100 to a new location, the coil electrodes may be used to perform another function such as, for example, to record measurements at such locations, perform ablation, etc. Further, for example, such measurements may include electrical activation measurements.

Figure 14A:
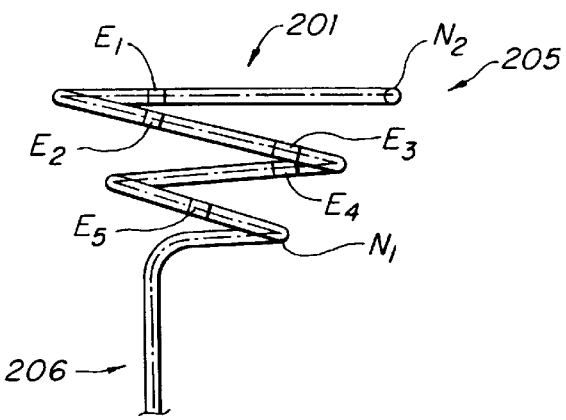
FIGS. 14A–14C are illustrations relating to an alternative tapered spring-like multiple, electrode catheter.
Figure 14B:
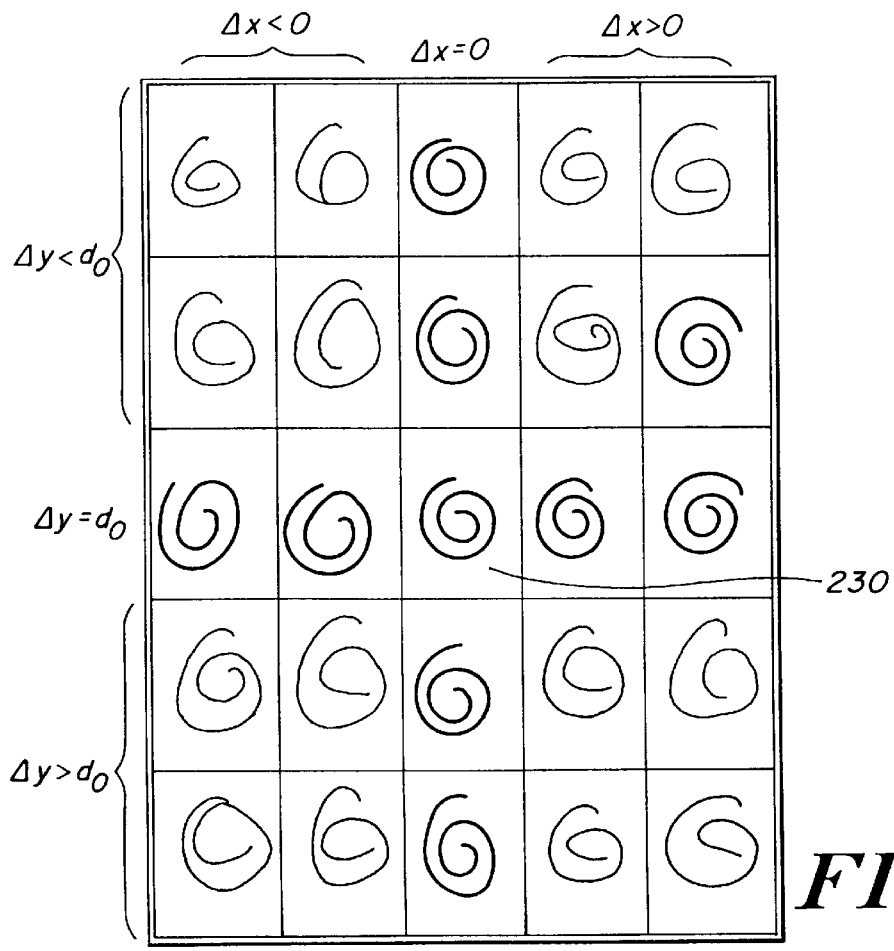
Figure 14C:
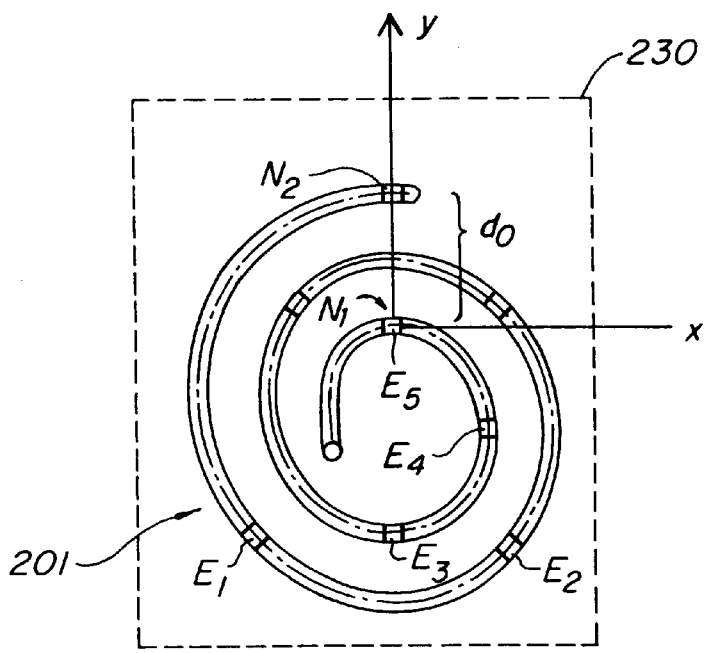

Another particular embodiment of a catheter 200 is shown in FIGS. 14A–14C and shall be described along with a virtual navigation method of determining locations for virtually navigable coil electrodes distributed along a length thereof. Like the illustrative example described above with reference to FIGS. 1–8, wherein the location of the virtually navigable electrode elements $E_1$–$E_n$ are determined using a lookup table addressable by delta calculations based on the positional coordinates (x, y, z) and angular orientation data ($\theta, \phi$) for the navigated electrode elements $N_1-N_n$, the location data for virtually navigable coil electrodes $E_1-E_5$ distributed along end length 201 of catheter 200 (FIGS. 14A–14C) are also determined based on experimental data regarding the displacement of the end length 201 of the catheter 200 from a baseline configuration.

As shown in FIG. 14A, catheter 200 includes an end length 201 that takes a generally tapered spring-like shape. The tapered spring-like end length 201 when utilized is pressed into a substantially flat end section lying in a single plane, e.g., x–y plane. For example, the catheter 200 may be positioned against a wall of a heart chamber or other vessel into generally a single plane when used within the navigational domain.

The end length 201 has two navigated coils affixed thereto, $N_2$ at the distal end 205 and $N_1$ at a proximal end 206. Virtually navigable coils $E_1-E_5$ are distributed between the coils $N_2$ and $N_1$ and along the end length 201. When this end section gets pressed into a single plane, e.g., against a chamber wall, it gets distorted in an unknown manner as shown by the various shapes shown in the array of FIG. 14B. The central diagram 230 of the array shown in FIG. 14B represents the end section 201 ideally pressed against a wall generally perpendicular to the axis of the tapered spring-like shape. This central diagram 230 is shown in further detail in FIG. 14C. As shown therein, the end section 201 in its ideal baseline position has navigated coil electrodes $N_2$ and $N_1$ at baseline positions, e.g., $N_2$ at $x_2=0$ and $y_2=d_0$; and $N_1$ at $x_1=0$ and $y_1=0$.

The method of navigating the multiple electrode catheter 200 includes the use of the locations of the navigated coil electrodes $N_1$ and $N_2$ to determine the locations for virtually navigable electrode elements $E_1-E_5$ distributed therebetween. The multiple electrode catheter 200 is pressed against a particular location within the navigational domain, e.g., a heart chamber wall. With the catheter 200 at this location and the end length 201 pressed into a generally single plane configuration, location data for the navigated coil electrodes $N_1$ and $N_2$ is attained by a method as described previously above. For example, positional coordinate data ($x_n$, $y_n$, $z_n$) and, optionally angular orientation data ($\theta_n$, $\phi_n$), for the navigated coil electrodes $N_1$ and $N_2$ is determined.

Figure 15:
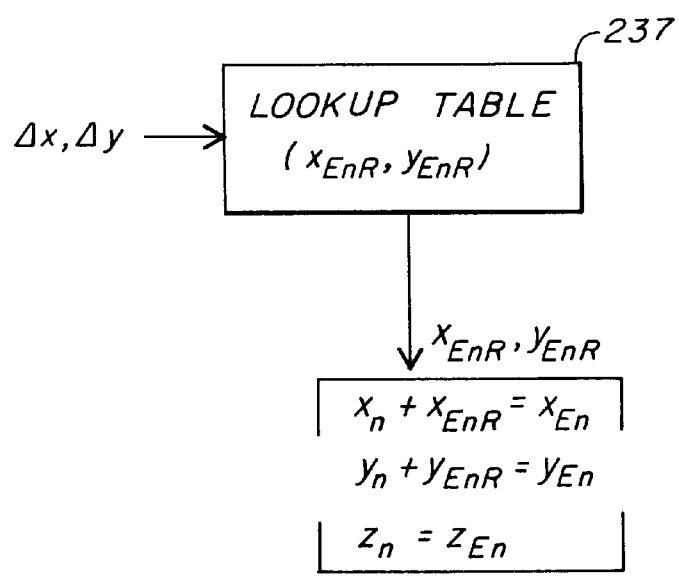
FIG. 15 is a block diagram showing the inputs and outputs of a lookup table used in an alternative navigation process similar to that of FIG. 6 for navigating the illustrative multiple electrode catheter shown in FIG. 14.

Thereafter, the location data for each of the virtually navigable coils $E_1-E_5$ is determined. The virtual navigation unit 19, used with the catheter 200 to determine the location data for the virtually navigable coil electrodes $E_1-E_5$ distributed along length 201 of catheter 200 using the location data of navigated coil electrodes $N_1$ and $N_2$, includes an empirical lookup table 237 as shown in FIG. 15. The lookup table 237, or any other suitable addressable memory apparatus operable for communication with the control unit 17, is used for storing sets of displacement coordinates for the virtually navigable electrode elements $E_1-E_5$. Each set of displacement coordinates represents the general deviation, determined experimentally, of the virtually navigable electrode elements $E_1-E_5$ from one of the navigated coil electrodes $N_1$ and $N_2$ when the navigated coil electrodes $N_1$ and $N_2$ are at a particular location relative to one another when the end length 201 of the catheter 200 has been pressed into a single plane and out of its baseline ideal configuration.

A setup similar to that of FIG. 8 is used for determining the sets of displacement coordinates for the lookup table 237. For example, navigated coil electrode $N_1$ is always designated as being at a position ($x_1=0$, $y_1=0$). With the end length flattened into all practical positions the navigated coil electrode $N_2$ is located at all practical locations relative to coil $N_1$. At each of such positions associated with a particular location of $N_2$ relative to the location of $N_1$, positional displacement coordinates ($x_{EnR}$, $y_{EnR}$) for the virtually navigable coils $E_1-E_5$ are measured and recorded into the lookup table 237 in a manner such that they are addressable by a delta location ($\Delta x$, $\Delta y$). The delta location is the difference value of each the x coordinates and y coordinates of $N_2$ relative to $N_1$. In the test setup, with the position of $N_1$ at ($x_1=0$, $y_1=0$), then the delta location ($\Delta x$, $\Delta y$) of $N_2$ relative to $N_1$ is equal to the location of $N_2$ or ($x_2$, $y_2$). FIG. 14B shows the various configurations for when $\Delta x$ and $\Delta y$ are greater than, less than, or equal to the respective baseline or ideal values. It should be apparent that the set of displacement coordinates may be averaged values measured for the same locations.

When the catheter 200 is flattened into a configuration within the navigational domain, the location of the virtually navigable electrode elements $E_1-E_5$ can be determined by comparing the location data for the two navigated coil electrodes $N_1$ and $N_2$. The difference between the positional coordinates of $N_1(x_1, y_1)$ and positional coordinates of $N_2(x_2, y_2)$ result in the delta location ($\Delta x$, $\Delta y$) for that particular position of the catheter 200 within the navigational domain. The delta location is then used to address the lookup table, or otherwise select from a memory, a set of displacement coordinates corresponding to this particular delta location as determined using the test setup.

The set of displacement coordinates may be provided from the lookup table in serial or parallel form as previously described with reference to FIG. 7. The displacement coordinates ($x_{EnR}$, $y_{EnR}$) for each of the virtually navigable coils are then added to the positional coordinates of $N_1(x_1, y_1, z_1)$ resulting in the virtual determination of the location of the virtually navigable coil electrodes. For example, $x_{E1R}$ is added to $x_1$ to obtain the x coordinate $x_{E1}$, and the y coordinate is added in the same manner. The z coordinate $z_{E1}$ will be the same as the end length is pressed into a single plane. Likewise, the location of the other virtually navigable coils are determined in substantially the same manner. It should be readily apparent that the lookup technique may be implemented in various manners and that the above process is for illustration only.

The preceding specific embodiments are illustrative of the practice of the invention. It is to be understood, however, that other expedients known to those skilled in the art or disclosed herein, may be employed without departing from the scope of the appended claims.

What is claimed is:

1. A method for navigating a catheter within a navigational domain, the method comprising the steps of:

providing a catheter including a plurality of locatable electrode elements distributed along and affixed to a length of the catheter, the plurality of locatable electrode elements including at least two navigated electrode elements and one or more virtually navigable electrode elements located relative to the at least two navigated electrode elements;

providing location data for the at least two navigated electrode elements; and determining location data for the one or more virtually navigable electrode elements as a function of the location data for the at least two navigated electrode elements.

2. The method according to claim 1, wherein the determination step includes the steps of:

providing a plurality of sets of displacement coordinates for the one or more virtually navigable electrode elements, each of the sets of displacement coordinates corresponding to a specific relative location between a selected navigated electrode element of the at least two navigated electrode elements and one or more other navigated electrode elements of the at least two navigated electrode elements; and determining the location data for the one or more of the virtually navigable electrode elements as a function of a set of displacement coordinates corresponding to a specific relative location of the at least two navigated electrode elements as represented by the location data for the at least two navigated electrode elements.

3. The method according to claim 2, wherein each of the sets of displacement coordinates represents a difference between coordinates of each of the one or more virtually navigable electrode elements and coordinates of the selected navigated electrode element of the at least two navigated electrode elements, and further wherein the step of determining the location data for the one or more virtually navigable electrode elements includes adding the set of displacement coordinates corresponding to the specific relative location to the coordinates of the selected navigated electrode element.

4. The method according to claim 3, wherein the determination step further includes comparing the location data for the selected navigated electrode element relative to the location data for the one or more other navigated electrode elements resulting in the specific relative location of the at least two navigated electrode elements, and further wherein the set of displacement coordinates for the one or more virtually navigable electrode elements is determined as a function of the specific relative location.

5. The method according to claim 2, wherein the step of providing the plurality of sets of displacement coordinates includes the steps of:

holding the location of one of the navigated electrode elements at a fixed location and moving a second navigated electrode element to a plurality of locations;

measuring the locations of the one or more virtually navigable electrode elements when the second navigated electrode element is at each of the plurality of locations; and generating the plurality of sets of displacement coordinates based on the measured locations of the one or more virtually navigable electrode elements.

6. The method according to claim 1, wherein the plurality of locatable electrode elements include a plurality of electrically conductive coils distributed along and affixed to the length of the catheter, the length being elongated and steerable into a plurality of configurations, and further wherein the plurality of coils include at least two navigated coils separated along the length of the catheter and one or more separated virtually navigable coils located along or near an intervening portion of the length of the catheter lying between the at least two navigated coils.

7. The method according to claim 6, wherein the step of providing the location data includes the step of providing orientation data of the orientation of the at least two navigated coils in the navigational domain and positional coordinate data of the at least two navigated coils in the navigational domain, and further wherein the determining step includes the step of determining positional coordinate data for the one or more virtually navigable coils as a function of the orientation data and the positional coordinate data of the at least two navigated coils.

8. The method according to claim 7, wherein the determination step includes the steps of:

providing a plurality of sets of displacement coordinates for the one or more virtually navigable coils, each of the sets of displacement coordinates corresponds to a specific relative location between a selected navigated coil of the at least two navigated coils and one or more other navigated coils of the at least two navigated coils and further wherein each of the sets of displacement coordinates represents a difference between the positional coordinate data of each of the one or more virtually navigable coils and the positional coordinate data of the selected navigated coil;

comparing the positional coordinate data and orientation data for the selected navigated coil to the positional location data and orientation data for one or more other navigated coils resulting in the specific relative location of the at least two navigated coils; and determining the set of displacement coordinates for the one or more virtually navigable coils as a function of the specific relative location of the at least two navigated coils resulting from the comparison; and adding the set of displacement coordinates for the one or more navigable coils corresponding to the specific relative location to the positional coordinate data of the selected navigated coil.

9. The method according to claim 1, wherein one or more of the navigated electrode elements are one of electrically conductive coils and electrically conductive bands equipped with colocated navigation coils.

10. The method according to claim 9, wherein one of the one or more virtually navigable electrode elements is an electrically conductive band.

11. The method according to claim 1, wherein at least one of the locatable electrode elements are operable for performing one of ablation, sensing electrograms, making temperature measurements, magnetic sensing for use in providing location data for the at least two navigated electrode elements, or transmitting signals for use in providing location data for the at least two navigated electrode elements.

12. The method according to claim 11, wherein the at least two navigated electrode elements are operable for magnetic sensing for use in providing location data for the at least two navigated electrode elements.

13. The method according to claim 1, wherein the one or more virtually navigable electrode elements are distributed and affixed to an intervening portion of the length of the catheter between the at least two navigated electrode elements.

14. The method according to claim 13, wherein at least one of the one or more virtually navigable electrode elements is affixed to the length of the catheter near one of the navigated electrode elements but outside of the intervening portion.

15. The method according to claim 1, wherein at least one of the one or more virtually navigable electrode elements is affixed to the length of the catheter near one of the navigated electrode elements but outside of an intervening portion of the catheter between the at least two navigated electrode elements.

16. The method according to claim 1, wherein the method further includes the step of steering the length of the catheter into one or more shapes, and further wherein the steps of providing location data for the at least two navigated electrode elements and determining of the location data for the one or more virtually navigable electrode elements are performed for each of the one or more shapes.

17. The method according to claim 1, wherein the catheter is steerable into one of a plurality of configurations with the length of the catheter taking the form of a shape definable by the location data of the at least two navigated electrode elements, and further wherein the determination step includes the step of determining the location data for the one or more virtually navigable electrode elements as a function of the defined shape and data representative of a displacement of the one or more virtually navigable electrode elements relative to a selected navigated electrode element of the at least two navigated electrode elements.

18. The method according to claim 17, wherein the locatable electrode elements include a plurality of electrically conductive coils distributed along and affixed to the length of the catheter, the plurality of coils including at least two navigated coils separated by a predetermined distance along the length of the catheter and one or more virtually navigable coils located at a predetermined distance along the length of the catheter from a selected one of the at least two navigated coils, further wherein the location data for the navigated coils includes orientation data of the orientation of the at least two navigated coils in the navigational domain and positional coordinate data of the at least two navigated coils in the navigational domain, and further wherein the determining step includes the step of determining positional coordinate data for the one or more virtually navigable coils as a function of the orientation data and the positional coordinate data of the at least two navigated coils and the predetermined distance along the catheter of the one or more virtually navigable coils from the selected navigated coil of the at least two navigated coils.

19. The method according to claim 18, wherein determining step includes the steps of:

calculating parameters of a helix that defines an intervening section of the length of the catheter lying between the at least two navigated coils as function of the orientation data and positional coordinate data of the at least two navigated coils; and determining the positional coordinate data for the virtually navigable coils using the helix defining the intervening section and the predetermined distance of the one or more virtually navigable coils from at least one of the at least two navigated coils.

20. The method according to claim 1, wherein the length of the catheter is in a tapered spring-like shape and when utilized within the navigational domain is generally flattened into a spiral-like element lying generally within a single plane, wherein the at least two navigated electrode elements are separated along the length of the catheter and the one or more virtually navigable electrode elements are located along or nearby an intervening portion of the length of the catheter lying between the at least two navigated electrode elements, and further wherein the step of providing the location data includes the step of providing positional coordinate data of at least two navigated electrode elements in the navigational domain and the determining step includes the step of determining positional coordinate data for the one or more virtually navigable electrode elements as a function of the positional coordinate data of the at least two navigated electrode elements.

21. The method according to claim 20, wherein the determination step includes the steps of:

providing a plurality of sets of displacement coordinates for the one or more virtually navigable electrode elements, each of the sets of displacement coordinates generally representing a coordinate displacement of the one or more virtually navigable coils relative to a selected navigated electrode element of the at least two navigated electrode elements when the at least two navigated electrode elements are at a particular location relative to one another in the single plane;

comparing positional coordinate data for the selected navigated electrode element relative to location data for one or more other navigated electrode elements resulting in a positional coordinate difference between the locations of the at least two navigated electrode elements;

selecting a set of displacement coordinates for the one or more virtually navigable electrode elements as a function of the positional coordinate difference; and determining location data for the one or more virtually navigable electrode elements based on the selected set of displacement coordinates and the location data of the selected navigated electrode element.

22. The method according to claim 21, wherein the step of providing the plurality of sets of displacement coordinates includes the steps of:

repeatedly flattening the catheter into the single plane;

measuring the locations of the one or more virtually navigable electrode elements relative to the selected navigated electrode element each time the catheter is flattened and the one or more other navigated electrode elements are at a particular coordinate position within the single plane relative to the selected navigated electrode element; and generating the plurality of sets of displacement coordinates based on the measured locations of the one or more virtually navigable electrode elements and the particular coordinate position of the one or more navigated electrode elements relative to the selected navigated electrode element.

23. A system for navigating a catheter within a navigational domain, the system comprising:

a catheter having a plurality of locatable electrode elements distributed along and affixed to a length of the catheter, the plurality of locatable electrode elements including at least two navigated electrode elements and one or more virtually navigable electrode elements located along or near an intervening portion of the length between the at least two navigated electrode elements;

one or more transmitters to project magnetic fields into the navigational domain sufficient to induce signal values within the at least two navigated electrode elements representative of the location of the at least two navigated electrode elements within the navigational domain; and a controller for generating location data from the induced signal values for the at least two navigated electrode elements and for determining location data for the one or more virtually navigable electrode elements as a function of the location data for the at least two navigated electrode elements.

24. The system according to claim 23, wherein the controller includes memory to store a plurality of sets of displacement coordinates for the one or more virtually navigable electrode elements, each of the sets of displacement coordinates representative of the coordinate displacement of the one or more virtually navigable electrode elements from a selected navigated electrode element of the at least two navigated electrode elements when the at least two navigated electrode elements are at a particular relative position to one another.

25. The system according to claim 24, wherein the controller further includes means for addressing the memory based on a particular relative location of the at least two navigated electrode elements as represented by the location data for the at least two navigated electrode elements to select a set of displacement coordinates for the one or more virtually navigable electrode elements corresponding to the particular relative location.

26. The system according to claim 25, wherein the plurality of locatable electrode elements are distributed along and affixed to the length of the catheter, include at least two navigated electrode elements equipped with a colocated magnetic sensing component separated along the length of the catheter and one or more virtually navigable electrode elements located along or near an intervening portion of the length of the catheter lying between the at least two navigated electrode elements.

27. The system according to claim 25, wherein the location data includes orientation data of the orientation of the at least two navigated electrode elements in the navigational domain and positional coordinate data of the at least two navigated electrode elements in the navigational domain, and further wherein the controller determines positional coordinate data for the one or more virtually navigable electrode elements and orientation data of the orientation of the one or more navigable electrode elements as a function of the orientation data and the positional coordinate data of the at least two navigated electrode elements.

28. The system according to claim 27, wherein the controller includes:

memory to store a plurality of sets of displacement coordinates for the one or more virtually navigable electrode elements, each of the sets of displacement coordinates corresponds to a specific relative location between a selected navigated electrode element of the at least two navigated electrode element and one or more other navigated electrode element of the at least two navigated electrode elements, and further wherein each of the sets of displacement coordinates represents a difference between the positional coordinate data of each of the one or more virtually navigable electrode elements and the positional coordinate data of the selected navigated electrode element;

means for comparing the positional coordinate data and orientation data for the selected navigated electrode element to the positional location data and orientation data for the one or more other navigated electrode elements resulting in a specific relative location of the at least two navigated electrode elements; and means for determining the set of displacement coordinates for the one or more virtually navigable electrode elements as a function of the specific relative location of the at least two navigated electrode elements resulting from the comparison; and means for adding the set of displacement coordinates for the one or more virtually navigable electrode elements corresponding to the specific relative location to the positional coordinate data of the selected navigated electrode element.

29. The system according to claim 23, wherein the catheter is steerable into one of a plurality of configurations with the length of the catheter taking the form of a shape definable by the location data of the at least two navigated electrode elements, and further wherein the controller includes means for determining the location data for the one or more virtually navigable electrode elements as a function of the defined shape and data representative of a displacement of the one or more virtually navigable electrode elements relative to a selected navigated electrode element of the at least two navigated electrode elements.

30. The system according to claim 29, wherein the location data for the navigated electrode elements includes orientation data of the orientation of the at least two navigated electrode elements in the navigational domain and positional coordinate data of the at least two navigated electrode elements in the navigational domain, and further wherein the determination means includes means for determining positional coordinate data for the one or more virtually navigable electrode elements as a function of the orientation data and the positional coordinate data of the at least two navigated electrode elements and the predetermined distance along the catheter of the one or more virtually navigable electrode elements from the selected navigated electrode element of the at least two navigated electrode elements.

31. The system according to claim 30, wherein determination means further includes the steps of:

calculating parameters of a helix that defines an intervening section of the length of the catheter lying between the at least two navigated electrode elements as function of the orientation data and positional coordinate data of the at least two navigated electrode elements; and determining the positional coordinate data for the virtually navigable electrode elements using the helix defining the intervening section and the predetermined distance of the one or more virtually navigable electrode elements from the selected navigated electrode element.

32. The system according to claim 23, wherein at least one of the locatable electrode elements are operable for performing one of ablation, sensing electrograms, making temperature measurements, magnetic sensing for use in providing location data for the at least two navigated electrode elements, or transmitting signals for use in providing location data for the at least two navigated electrode elements.

33. The system according to claim 23, wherein the at least two navigated electrode elements are operable for magnetic sensing for use in providing location data for the at least two navigated electrode elements.

34. The system according to claim 23, wherein the system further includes means for steering the length of the catheter into one or more shapes.

* * * * *